United States Patent
Garvey

(10) Patent No.: US 7,345,053 B2
(45) Date of Patent: Mar. 18, 2008

(54) NITROSATED AND NITROSYLATED RAPAMYCIN COMPOUNDS, COMPOSITIONS AND METHODS OF USE

(75) Inventor: David S. Garvey, Dover, MA (US)

(73) Assignee: Nitromed, Inc., Lexington, MA (US)

( * ) Notice: Subject to any disclaimer, the term of this patent is extended or adjusted under 35 U.S.C. 154(b) by 284 days.

(21) Appl. No.: 11/135,308

(22) Filed: May 24, 2005

(65) Prior Publication Data

US 2005/0209266 A1    Sep. 22, 2005

Related U.S. Application Data

(63) Continuation of application No. PCT/US03/39562, filed on Dec. 15, 2003.

(60) Provisional application No. 60/433,595, filed on Dec. 16, 2002, provisional application No. 60/513,215, filed on Oct. 23, 2003.

(51) Int. Cl.
C07D 498/18   (2006.01)
A61K 31/445   (2006.01)

(52) U.S. Cl. ................... 514/291; 540/456
(58) Field of Classification Search ............... 540/456; 514/291

See application file for complete search history.

(56) References Cited

U.S. PATENT DOCUMENTS

| | | | |
|---|---|---|---|
| 5,120,842 A | 6/1992 | Failli et al. | |
| 5,527,907 A | 6/1996 | Or et al. | |
| 6,153,252 A | 11/2000 | Hossainy et al. | |
| 6,273,913 B1 | 8/2001 | Wright et al. | |

FOREIGN PATENT DOCUMENTS

| | | |
|---|---|---|
| EP | 0 950 386 A2 | 10/1999 |
| WO | WO 92/05179 | 4/1992 |
| WO | WO 93/18043 | 9/1993 |
| WO | WO 94/02136 | 2/1994 |
| WO | WO 94/02137 | 2/1994 |
| WO | WO 94/02485 | 2/1994 |
| WO | WO 94/09010 | 4/1994 |
| WO | WO 94/10176 | 5/1994 |
| WO | WO 94/18208 | 8/1994 |
| WO | WO 95/04060 | 2/1995 |
| WO | WO 95/04738 | 2/1995 |
| WO | WO 95/14023 | 5/1995 |
| WO | WO 95/14696 | 6/1995 |
| WO | WO 95/14697 | 6/1995 |
| WO | WO 95/16691 | 6/1995 |
| WO | WO 95/22972 | 8/1995 |
| WO | WO 95/28406 | 10/1995 |
| WO | WO 95/34565 | 12/1995 |
| WO | WO 96/06847 | 3/1996 |
| WO | WO 96/16967 | 6/1996 |
| WO | WO 96/17845 | 6/1996 |
| WO | WO 96/41807 | 12/1996 |
| WO | WO 98/09970 | 3/1998 |
| WO | WO 98/09972 | 3/1998 |
| WO | WO 01/34816 A1 | 5/2001 |
| WO | WO 01/87263 A2 | 11/2001 |
| WO | WO 01/87342 A2 | 11/2001 |
| WO | WO 01/87372 A1 | 11/2001 |
| WO | WO 01/87373 A1 | 11/2001 |
| WO | WO 01/87374 A1 | 11/2001 |
| WO | WO 01/87376 A1 | 11/2001 |
| WO | WO 01/97809 A2 | 12/2001 |
| WO | WO 02/36054 A1 | 5/2002 |

*Primary Examiner*—Bruck Kifle
(74) *Attorney, Agent, or Firm*—Wilmer Cutler Pickering Hale and Dorr, LLP

(57) ABSTRACT

The invention describes novel nitrosated and/or nitrosylated rapamycin compounds, and novel compositions comprising at least one nitrosated and/or nitrosylated rapamycin compound, and, optionally, at least one nitric oxide donor compound. The invention also provides novel compositions comprising at least one rapamycin compound and at least one nitric oxide donor compound and/or at least one therapeutic agent. The compounds and compositions of the invention can also be bound to a matrix. The invention also provides methods for treating and/or preventing cardiovascular diseases, for the prevention of platelet aggregation and platelet adhesion caused by the exposure of blood to a medical device, for treating and/or preventing pathological conditions resulting from abnormal cell proliferation; transplantation rejections; autoimmune, inflammatory, proliferative, hyperproliferative or vascular diseases; for reducing scar tissue or for inhibiting wound contraction, particularly the prophylactic and/or therapeutic treatment of restenosis by administering nitrosated and/or nitrosylated rapamycin compounds or rapamycin compounds in combination with nitric oxide donors that are capable of releasing nitric oxide or indirectly delivering or transferring nitric oxide to targeted sites under physiological conditions.

3 Claims, No Drawings

NITROSATED AND NITROSYLATED RAPAMYCIN COMPOUNDS, COMPOSITIONS AND METHODS OF USE

RELATED APPLICATIONS

This application is a continuation of PCT/US2003/039562, filed Dec. 15, 2003, which claims priority under 35 USC § 119 to U.S. Provisional Application No. 60/433,595 filed Dec. 16, 2002, and U.S. Provisional Application No. 60/513,215 filed Oct. 23, 2003.

FIELD OF THE INVENTION

The invention describes novel nitrosated and/or nitrosylated rapamycin compounds, and novel compositions comprising at least one nitrosated and/or nitrosylated rapamycin compound, and, optionally, at least one nitric oxide donor compound. The invention also provides novel compositions comprising at least one rapamycin compound and at least one nitric oxide donor compound and/or at least one therapeutic agent. The compounds and compositions of the invention can also be bound to a matrix. The invention also provides methods for treating and/or preventing cardiovascular diseases, for the prevention of platelet aggregation and platelet adhesion caused by the exposure of blood to a medical device, for treating and/or preventing pathological conditions resulting from abnormal cell proliferation; transplantation rejections; autoimmune, inflammatory, proliferative, hyperproliferative or vascular diseases; for reducing scar tissue or for inhibiting wound contraction, particularly the prophylactic and/or therapeutic treatment of restenosis by administering nitrosated and/or nitrosylated rapamycin compounds or rapamycin compounds in combination with nitric oxide donors that are capable of releasing nitric oxide or indirectly delivering or transferring nitric oxide to targeted sites under physiological conditions.

BACKGROUND OF THE INVENTION

Endothelium-derived relaxing factor (EDRF) is a vascular relaxing factor secreted by the endothelium and is important in the control of vascular tone, blood pressure, inhibition of platelet aggregation, inhibition of platelet adhesion, inhibition of mitogenesis, inhibition of proliferation of cultured vascular smooth muscle, inhibition of leukocyte adherence and prevention of thrombosis. EDRF has been identified as nitric oxide (NO) or a closely related derivative thereof (Palmer et al, *Nature*, 327:524-526 (1987); Ignarro et al, *Proc. Natl. Acad. Sci. USA*, 84:9265-9269 (1987)).

Removal of the endothelium is a potent stimulus for neointimal proliferation, a common mechanism underlying the restenosis of atherosclerotic vessels after balloon angioplasty (Liu et al., *Circulation*, 79:1374-1387 (1989); Fems et al., *Science*, 253:1129-1132 (1991)). Balloon arterial injury results in endothelial denudation and subsequent regrowth of dysfunctional endothelium (Saville, *Analyst*, 83:670-672 (1958)) that may contribute to the local smooth muscle cell proliferation and extracellular matrix production that result in reocclusion of the arterial lumen. Nitric oxide dilates blood vessels (Vallance et al., *Lancet*, 2:997-1000 (1989)), inhibits platelet activation and adhesion (Radomski et al., *Br. J Pharmacol*, 92:181-187 (1987)), and nitric oxide limits the proliferation of vascular smooth muscle cells in vitro (Garg et al., *J. Clin. Invest.*, 83:1774-1777 (1986)). Similarly, in animal models, suppression of platelet-derived mitogens decreases intimal proliferation (Fems et al., *Science*, 253: 1129-1132 (1991)). The potential importance of endothelium-derived nitric oxide in the control of arterial remodeling after injury is further supported by recent preliminary reports in humans suggesting that systemic nitric oxide donors reduce angiographic restenosis six months after balloon angioplasty (The ACCORD Study Investigators, *J. Am. Coil. Cardiol.* 23:59A. (Abstr.) (1994)).

Another aspect of restenosis may simply be mechanical, e.g., caused by the elastic rebound of the arterial wall and/or by dissections in the vessel wall caused by the angioplasty procedure. These mechanical problems have been successfully addressed by the use of stents to tack-up dissections and prevent elastic rebound of the vessel thereby reducing the level of re-occlusion for many patients. The stent is typically inserted by catheter into a vascular lumen and expanded into contact with the diseased portion of the arterial wall, thereby providing internal support for the lumen. No material has, however, been developed that matches the blood-compatible surface of the endothelium. In fact, in the presence of blood and plasma proteins, artificial surfaces are an ideal setting for platelet deposition (Salzman et al, *Phil. Trans. R. Soc. Lond.*, B294:389-398 (1981)). Exposure of blood to an artificial surface initiates reactions that lead to clotting or platelet adhesion and aggregation. Within seconds of blood contact, the artificial surface becomes coated with a layer of plasma proteins which serves as a new surface to which platelets readily adhere, become activated, and greatly accelerate thrombus formation (Forbes et al, *Brit. Med. Bull.*, 34(2):201-207 (1978)).

Despite considerable efforts to develop nonthrombogenic materials, no synthetic material has been created that is free from this effect. In addition, the use of anticoagulant and platelet inhibition agents has been less than satisfactory in preventing adverse consequences resulting from the interaction between blood and artificial surfaces. Consequently, a significant need exists for the development of additional methods for preventing platelet deposition and thrombus formation on artificial surfaces.

There is a need in the art for effective methods of preventing and treating cardiovascular diseases and disorders, particularly, restenosis and atherosclerosis. The invention is directed to these, as well as other, important ends.

SUMMARY OF THE INVENTION

The invention describes novel nitrosated and/or nitrosylated rapamycin compounds and methods for preventing and/or treating cardiovascular diseases and disorders by administering one or more nitrosated and/or nitrosylated rapamycin compounds that are capable of releasing a therapeutically effective amount of nitric oxide to a targeted site effected by a cardiovascular disease or disorder. Preferably, the methods of the invention are used for treating and/or preventing restenosis and atherosclerosis.

One embodiment of the invention provides novel nitrosated and/or nitrosylated rapamycin compounds. The rapamycin compounds can be nitrosated and/or nitrosylated through one or more sites such as, oxygen (hydroxyl condensation), sulfur (sulfhydryl condensation) and/or nitrogen. The invention also provides compositions comprising a therapeutically effective amount of such compounds in a pharmaceutically acceptable carrier.

Another embodiment of the invention provides compositions comprising a therapeutically effective amount of at least one rapamycin compound, that is optionally substituted with at least one NO and/or $NO_2$ group (i.e., nitrosylated and/or nitrosated), and at least one compound that donates, transfers or releases nitrogen monoxide as a charged species, i.e., nitrosonium (NO$^+$) or nitroxyl (NO–), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Yet another embodiment of the invention provides compositions comprising a therapeutically effective amount of at least one rapamycin compound, that is optionally substituted with at least one NO and/or NO$_2$ group (i.e., nitrosylated and/or nitrosated), at least one therapeutic agent, and, optionally, at least one compound that donates, transfers or releases nitrogen monoxide as a charged species, i.e., nitrosonium (NO$^+$) or nitroxyl (NO–), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Another embodiment of the invention describes compositions and methods for making compositions comprising at least one rapamycin compound, that is optionally substituted with at least one NO and/or NO$_2$ group (i.e., nitrosylated and/or nitrosated), and, optionally, at least one compound that donates, transfers or releases nitric oxide and/or stimulates endogenous production of nitric oxide or EDRF in vivo and/or is a substrate for nitric oxide synthase and/or at least one therapeutic agent, that are bound to a natural or synthetic matrix, which can be applied with specificity to a biological site of interest. For example, the matrix containing the compounds or compositions of the invention (e.g. nitrosated and/or nitrosylated rapamycin compounds) can be used to coat the surface of a medical device that comes into contact with blood (including blood components, blood products and the like), vascular or non-vascular tissue.

Yet another embodiment of the invention provides methods for treating and/or preventing cardiovascular diseases and disorders, by administering to a patient in need thereof a therapeutically effective amount of at least one nitrosated and/or nitrosylated rapamycin compound and, optionally, at least one compound that donates, transfers or releases nitric oxide as a charged species, i.e., nitrosonium (NO$^+$) or nitroxyl (NO–), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one therapeutic agent. Alternatively, the methods for treating and/or preventing cardiovascular diseases and disorders, can comprise administering a therapeutically effective amount of at least one nitrosated and/or nitrosylated rapamycin compound, at least one therapeutic agent, and, optionally, at least one compound that donates, transfers or releases nitric oxide as a charged species, i.e., nitrosonium (NO$^+$) or nitroxyl (NO–), or as the neutral species, nitric oxide (NO.), and/or stimulates endogenous production of nitric oxide or EDRF in vivo and/or is a substrate for nitric oxide synthase. Alternatively the methods can comprise administering at least one rapamycin compound and at least one NO donor, and, optionally, at least one therapeutic agent. The rapamycin compound that is optionally nitrosated and/or nitrosylated, nitric oxide donors, and/or therapeutic agents can be administered separately or as components of the same composition in one or more pharmaceutically acceptable carriers.

Yet another embodiment of the invention describes methods for the prevention of platelet aggregation and platelet adhesion caused by the exposure of blood to a medical device by incorporating at least one nitrosated and/or nitrosylated rapamycin compound that is capable of releasing a therapeutically effective amount of nitric oxide, into and/or on the portion(s) of the medical device that come into contact with blood (including blood components and blood products), vascular or non-vascular tissue. The methods can further comprise incorporating at least one compound that donates, transfers or releases nitric oxide, and/or stimulates endogenous production of nitric oxide or EDRF in vivo and/or is a substrate for nitric oxide synthase, and, optionally, at least one therapeutic agent into and/or on the portion(s) of the medical device that come into contact with blood, vascular or non-vascular tissue. Alternatively the methods can comprise incorporating at least one rapamycin compound and at least one NO donor, and, optionally, at least one therapeutic agent, into and/or on the portion(s) of the medical device that come into contact with blood (including blood components and blood products), vascular or non-vascular tissue.

Another embodiment of the invention relates to the systemic and/or local administration of at least one rapamycin compound, that is optionally substituted with at least one NO and/or NO$_2$ group, and, optionally, at least one therapeutic agent and/or at least one nitric oxide donor, to treat injured tissue, such as, damaged blood vessels.

The invention also provides methods using the compounds and compositions described herein to prevent or treat pathological conditions resulting from abnormal cell proliferation; transplantation rejections; autoimmune, inflammatory, proliferative, hyperproliferative or vascular diseases; for reducing scar tissue or for inhibiting wound contraction by administering to a patient in need thereof a therapeutically effective amount of at least one of the compounds and/or compositions described herein. In these methods, the rapamycin compound that is optionally nitrosated and/or nitrosylated, nitric oxide donors and therapeutic agents can be administered separately or as components of the same composition in one or more pharmaceutically acceptable carriers.

These and other aspects of the invention are described in detail herein.

DETAILED DESCRIPTION OF THE INVENTION

As used throughout the disclosure, the following terms, unless otherwise indicated, shall be understood to have the following meanings.

"Cardiovascular disease or disorder" refers to any cardiovascular disease or disorder known in the art, including, but not limited to, restenosis, coronary artery disease, atherosclerosis, atherogenesis, cerebrovascular disease, angina, (particularly chronic, stable angina pectoris), ischemic disease, congestive heart failure, pulmonary edema associated with acute myocardial infarction, aneurysm, thrombosis, hypertension (e.g. pulmonary hypertension, low-renin hypertension, salt-sensitive hypertension, low-renin, salt-sensitive hypertension, thromboembolic pulmonary hypertension; pregnancy-induced hypertension; renovascular hypertension; hypertension-dependent end-stage renal disease, hypertension associated with cardiovascular surgical procedures and the like), platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neointimal hyperplasia following percutaneous transluminal ccoronary angiograph, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. For these angioplasty procedures, restenosis occurs at a rate of about 30-60% depending upon the vessel location, lesion length and a number of other variables. Restenosis can also occur following a number of invasive surgical techniques, such as, for example, transplant surgery, vein grafting, coronary artery bypass surgery, endarterectomy, heart transplantation, ballon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as, growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery.

"Autoimmune, inflammatory, proliferative, hyperproliferative or vascular diseases" refers to any autoimmune, inflammatory, proliferative or hyperproliferative disease or disorder known in the art whether of a chronic or acute nature, including, but not limited to, rheumatoid arthritis, restenosis, lupus erythematosus, systemic lupus erythematosus, Hashimotos thyroiditis, myasthenia gravis, diabetes mellitus, uveitis, nephritic syndrome, multiple sclerosis; inflammatory skin diseases, such as, for example, psoriasis, dermatitis, contact dermatitis, eczema and seborrhea; surgical adhesion; tuberculosis; inflammatory lung diseases, such as, asthma, pneumoconiosis, chronic obstructive pulmonary disease, emphysema, bronchitis, nasal polyps and pulmonary fibrosis; inflammatory bowel disease, such as, Crohn's disease and ulcerative colitis; graft rejections; inflammatory diseases that affect or cause obstruction of a body passageway, such as, vasculitis, Wegener's granulomatosis and Kawasaki disease; inflammation of the eye, nose or throat, such as, neovascular diseases of the eye including neovascular glaucoma, proliferative diabetic retinopathy, retrolental fibroblasia, macular degeneration, reduction of intraocular pressure, corneal neovascularization, such as, corneal infections; immunological processes, such as, graft rejection and Steven-Johnson's syndrome, alkali bums, trauma and inflammation (of any cause); fungal infections, such as, for example, infections caused by *Candida, Trichophyton, Microsporum, Eepidermophyton, Cryptococcus, Aspergillus, Coccidiodes, Paracocciciodes, Histoplasma* or *Blastomyces* spp; food related allergies, such as, for example, migraine, rhinitis and eczema; vascular diseases, such as, arotic aneurysm. A description of inflammatory diseases can also be found in WO 92/05179, WO 98/09972, WO 98/24427, WO 99/62510 and U.S. Pat. No. 5,886,026, the disclosures of each of which are incorporated herein in their entirety.

"Pathological conditions resulting from abnormal cell proliferation" refers to any abnormal cellular proliferation of malignant or non-malignant cells in various tissues and/or organs, including but not limited to, muscle, bone, conjunctive tissues, skin, brain, lungs, sexual organs, lymphatic system, renal system, mammary cells, blood cells, liver, the digestive system, pancreas, thyroid, adrenal glands and the like. These pathological conditions can also include psoriasis; solid tumors; ovarian, breast, brain, prostate, colon, osesophageal, lung, stomach, kidney and/or testicular cancer; Karposi's sarcoma, cholangiocarcinoma; choriocarcinoma; neoblastoma; Wilm's tumor; Hodgkin's disease; melanomas; multiple myelomas; chronic lymphocytic leukemias, and acute or chronic granulocytic lymphomas. The treatment of "pathological conditions resulting from abnormal cell proliferation" includes, but is not limited to, reduction of tumor size, inhibition of tumor growth and/or prolongation of the survival time of tumor-bearing patients "Transplantation" refers to the transplant of any organ or body part, including but not limited to, heart, kidney, liver, lung, bone marrow, cornea and skin transplants.

"Artificial surface" refers to any natural or synthetic material contained in a device or apparatus that is in contact with blood, vasculature or other tissues.

"Blood" includes blood products, blood components and the like.

"Platelet adhesion" refers to the contact of a platelet with a foreign surface, including any artificial surface, such as, a medical device, as well as injured vascular or non-vascular surfaces, such as, collagen. Platelet adhesion does not require platelet activation. Unactivated, circulating platelets will adhere to injured vascular or non-vascular surfaces or artificial surfaces via binding interactions between circulating von Willdebrand factor and platelet surface glycoprotein Ib/IX.

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Passivation" refers to the coating of a surface which renders the surface non-reactive.

"Patient" refers to animals, preferably mammals, most preferably humans, and includes males and females, and children and adults.

"Therapeutically effective amount" refers to the amount of the compound and/or composition that is effective to achieve its intended purpose.

"Medical device" refers to any intravascular or extravascular medical devices, medical instruments, foreign bodies including implants and the like. Examples of intravascular medical devices and instruments include balloons or catheter tips adapted for insertion, prosthetic heart valves, sutures, surgical staples, synthetic vessel grafts, stents (e.g. Palmaz- Schatz, Wiktor, Crown, Mutlilink, GFX stents), stent grafts, vascular or non-vascular grafts, shunts, aneurysm fillers (including GDC, Guglilmi detachable coils), intraluminal paving systems, guide wires, embolic agents (for example, polymeric particles, spheres and liquid embolics), filters (for example, vena cava filters), drug pumps, arteriovenous shunts, artificial heart valves, artificial implants, foreign bodies introduced surgically into the blood vessels or at vascular or non-vascular sites, leads, pacemakers, implantable pulse generators, implantable cardiac defibrillators, cardioverter defibrillators, defibrillators, spinal stimulators, brain stimulators, sacral nerve stimulators, chemical sensors, breast implants, interventional cardiology devices, catheters, and the like. Examples of extravascular medical devices and instruments include plastic tubing, dialysis bags or membranes whose surfaces come in contact with the blood stream of a patient. The term "medical device" also includes bandages or any external device that can be applied directed to the skin.

"Antioxidant" refers to and includes any compound that can react and quench a free radical.

"Angiotensin converting enzyme (ACE) inhibitor" refers to compounds that inhibit an enzyme which catalyzes the conversion of angiotensin I to angiotensin II. ACE inhibitors include, but are not limited to, amino acids and derivatives thereof, peptides, including di- and tri-peptides, and antibodies to ACE which intervene in the renin-angiotensin system by inhibiting the activity of ACE thereby reducing or eliminating the formation of the pressor substance angiotensin II.

"Angiotensin II antagonists" refers to compounds which interfere with the function, synthesis or catabolism of angiotensin II. Angiotensin II antagonists include peptide compounds and non-peptide compounds, including, but not limited to, angiotensin II antagonists, angiotensin II receptor antagonists, agents that activate the catabolism of angiotensin II, and agents that prevent the synthesis of angiotensin I from angiotensin II. The renin-angiotensin system is involved in the regulation of hemodynamics and water and electrolyte balance. Factors that lower blood volume, renal perfusion pressure, or the concentration of sodium in plasma tend to activate the system, while factors that increase these parameters tend to suppress its function.

"Anti-hyperlipidemic drugs" refers to any compound or agent that has the effect of beneficially modifying serum cholesterol levels such as, for example, lowering serum low density lipoprotein (LDL) cholesterol levels, or inhibiting oxidation of LDL cholesterol, whereas high density lipoprotein (HDL) serum cholesterol levels may be lowered, remain the same, or be increased. Preferably, the anti-hyperlipidemic drug brings the serum levels of LDL cholesterol and HDL cholesterol (and, more preferably, triglyceride levels) to normal or nearly normal levels.

"Neutral endopeptidase inhibitors" refers to and includes compounds that are antagonists of the renin angiotensin aldosterone system including compounds that are dual inhibitors of neutral endopeptidases and angiotensin converting (ACE) enzymes.

"Renin inhibitors" refers to compounds which interfere with the activity of renin.

"Platelet reducing agents" refers to compounds that prevent the formation of a blood thrombus via any number of potential mechanisms. Platelet reducing agents include, but are not limited to, fibrinolytic agents, anti-coagulant agents and any inhibitors of platelet function. Inhibitors of platelet function include agents that impair the ability of mature platelets to perform their normal physiological roles (i.e., their normal function, such as, for example, adhesion to cellular and non-cellular entities, aggregation, release of factors such as growth factors) and the like.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 µM and a cyclooxygenase-1 $IC_{50}$ of greater than about 5 µM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Therapeutic agent" includes any therapeutic agent that can biologically stent a vessel and/or reduce or inhibit vascular remodeling and/or inhibit or reduce vascular or non-vascular smooth muscle proliferation following a procedural vascular trauma and includes the pro-drugs and pharmaceutical derivatives thereof including, but not limited to, the corresponding nitrosated and/or nitrosylated derivatives. Although nitric oxide donors have therapeutic activity, the term "therapeutic agent" does not include the nitric oxide donors described herein, since nitric oxide donors are separately defined.

"Nitric oxide donor compound" refers to any compound that

"Rapamycin compound" refers to a class of immunosuppressive compounds, or pharmaceutically acceptable salts thereof, and/or stereoisomers thereof, which contain the carbon core framework represented by Formula A or Formula B. The rapamycin compounds can be synthesized or produced by fermentation by a microorganism or fungus, such as, for example, *Streptomyces hygroscopicus, Streptomyces tsukubaensis*, and the like;

A

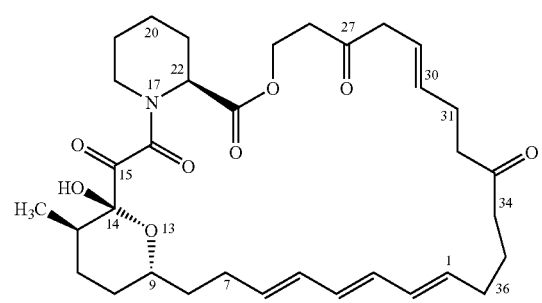

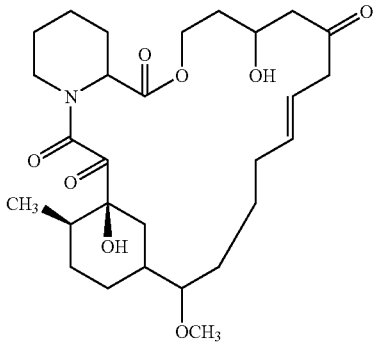
B

The term "rapamycin compounds" includes compounds that may be chemically or biologically modified and retain the immunosuppressive properties, including, but not limited to, esters, ethers, oximes, hydrazones and hydroxylamines of rapamycin, as well as rapamycin in which the function groups on the rapamycin nucleus have been modified, for example, through reduction or oxidation, and the like. Rapamycin compounds include, but are not limited to, rapamycin (also known as RAPA, Rapamune, Sirolimus, AY-22989 or NSC-226080), a 42-deoxy-42-(1H-tetrazol-1-yl)-rapamycin (also known as A 179578), 42-deoxy-42-(2H-tetrazol-1-yl)-rapamycin, 42-O-(2-hydroxyethyl)-rapamycin (also known as Certican, Everolimus, RAD, RAD 001 or SDZ-RAD), Tacrolimus, Ascomycin, as well as the compounds disclosed in U.S. Pat. Nos. 3,929,992, 4,316,885, 4,650,803, 5,023,263, 5,023,264, 5,100,883, 5,118,677, 5,118,678, 5,120,842, 5,130,307, 5,162,333, 5,177,203, 5,221,670, 5,233,036, 5,256,790, 5,258,389, 5,260,300, 5,262,423, 5,302,584, 5,362,718, 5,373,014, 5,378,836, 5,385,908, 5,385,909, 5,385,910, 5,389,639, 5,391,730, 5,411,967, 5,434,260, 5,463,048, 5,480,988, 5,480,989, 5,489,680, 5,491,772, 5,527,907, 5,551,413, 5,563,145, 5,665,772, 5,780,462, and in WO 92/05179, WO 93/18043, WO 94/18208, WO 94/02136, WO 94/02137, WO 94/02458, WO 94/09010, WO 94/10176, WO 95/04060, WO 95/04738, WO 95/14023, WO 95/14696, WO 95/14697, WO 95/16691, WO 95/22972, WO 95/28406, WO 95/34565, WO 96/06847, WO 96/16967, WO 96/41807, WO 96/17845, WO 98/09970, WO 98/09972, WO 01/34816, and WO 01/97809, the disclosures of each of which are incorporated by reference herein in their entirety. The immunosuppressive properties of a rapamycin compound can be determined using any of the routine methods and routine assays known to one skilled in the art, including, but not limited to, those disclosed in WO 95/28406, the disclosure of which is incorporated herein in its entirety.

"Prodrug" refers to a compound that is made more active in vivo.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of a therapeutically active compound and/or composition such that the blood levels of the therapeutically active compound are maintained within a desirable therapeutic range over an extended period of time. The sustained release formulation can be prepared using any conventional method known to one skilled in the art to obtain the desired release characteristics.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO–, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabicyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, 2,6-dioxabicyclo(3.3.0) octane, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetrahydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O-$, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S-$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to $=O$.

"Oxy" refers to $-O^-R_{77}^+$ wherein $R_{77}$ is an organic or inorganic cation.

"Oxime" refers to $=N-OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to $=N-N(R_{81})(R'_{81})$ wherein $R'_{81}$ is independently selected from $R_{81}$, and $R_{81}$ is as defined herein.

"Hydrazino" refers to $H_2N-N(H)-$.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to $-O-NO_2$.

"Nitrite" refers to $-O-NO$.

"Thionitrate" refers to $-S-NO_2$.

"Thionitrite" and "nitrosothiol" refer to $-S-NO$.

"Nitro" refers to the group $-NO_2$ and "nitrosated" refers to compounds that have been substituted therewith.

"Nitroso" refers to the group $-NO$ and "nitrosylated" refers to compounds that have been substituted therewith.

"Nitrile" and "cyano" refer to $-CN$.

"Halogen" or "halo" refers to iodine (I), bromine (Br), chlorine (Cl), and/or fluorine (F).

"Amino" refers to $-NH_2$, an alkylamino group, a dialkylamino group, an arylamino group, a diarylamino group, an alkylarylamino group or a heterocyclic ring, as defined herein.

"Alkylamino" refers to $R_{50}NH-$, wherein $R_{50}$ is an alkyl group, as defined herein. Exemplary alkylamino groups include methylamino, ethylamino, butylamino, cyclohexylamino, and the like.

"Arylamino" refers to $R_{55}NH-$, wherein $R_{55}$ is an aryl group, as defined herein.

"Dialkylamino" refers to $R_{52}R_{53}N-$, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N-$, wherein $R_{55}$ and $R_{60}$ are each independently an aryl group, as defined herein.

"Alkylarylamino or arylalkylamino" refers to $R_{52}R_{55}N-$, wherein $R_{52}$ is an alkyl group, as defined herein, and $R_{55}$ is an aryl group, as defined herein.

"Alkylarylalkylamino" refers to $R_{52}R_{79}N-$, wherein $R_{52}$ is an alkyl group, as defined herein, and $R_{79}$ is an arylalkyl group, as defined herein.

"Alkylcycloalkylamino" refers to $R_{52}R_{80}N-$, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to $-S-$.

"Sulfinyl" refers to $-S(O)-$.

"Methanthial" refers to $-C(S)-$.

"Thial" refers to $=S$.

"Sulfonyl" refers to $-S(O)_2^-$.

"Sulfonic acid" refers to $-S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to $-S(O)_2OR_{58}$, wherein $R_{58}$ is an alkyl group, an aryl group, or an aryl heterocyclic ring, as defined herein.

"Sulfonamido" refers to $-S(O)_2-N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S-$, wherein $R_{50}$ is an alkyl group, as defined herein (preferably a lower alkyl group, as defined herein).

"Arylthio" refers to $R_{55}S-$, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}-S(O)-$, wherein $R_{50}$ is an alkyl group, as defined herein.

"Alkylsulfonyl" refers to $R_{50}-S(O)_2-$, wherein $R_{50}$ is an alkyl group, as defined herein.

"Alkylsulfonyloxy" refers to $R_{50}-S(O)_2-O-$, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Arylsulfonyloxy" refers to $R_{55}$—S(O)$_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}$C(O)$R_{76}$— wherein $R_{51}$ is a hydrogen atom, an alkyl group, an aryl group or an arylheterocyclic ring, as defined herein and $R_{76}$ is oxygen or sulfur.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$, and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

The invention is directed to the treatment and/or prevention of cardiovascular diseases and disorders in patients by administering one or more rapamycin compounds that are linked (directly or indirectly) to one or more nitric oxide adducts. Preferably, the rapamycin compounds that are linked to one or more nitric oxide adducts are administered in the form of a pharmaceutical composition that further comprises a pharmaceutically acceptable carrier or diluent. The novel compounds and novel compositions of the invention are described in more detail herein.

In one embodiment, the invention describes rapamycin compounds comprising at least one NO group, at least one NO$_2$ group, or at least one NO and NO$_2$ group; a stereoisomer thereof and/or a pharmaceutically acceptable salt thereof, wherein the at least one NO group, the at least one NO$_2$ group, or the at least one NO and NO$_2$ group is linked to the rapamycin compound through an oxygen atom, a nitrogen atom or a sulfur atom.

In another embodiment, the invention describes nitrosated and/or nitrosylated rapamycin compounds and pharmaceutically acceptable salts thereof, and/or stereoisomers thereof, of Formula (I);

wherein the compound of Formula (I) is:

wherein:

$R^3$ is an oxygen, N—O$D^1$ or N—NH$D^1$;

$D^1$ is a hydrogen, V or K;

$D^2$ is a hydrogen, —CH$_3$, V or K;

$D^3$ is —O$D^1$, —O—CH$_2$—CH$_2$—O$D^1$,

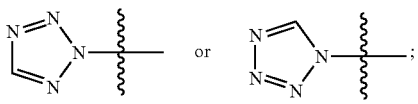

V is —NO or —NO$_2$;

K is —W$_a$-E$_b$-(C(R$_e$)(R$_f$))$_p$-E$_c$-(C(R$_e$)(R$_f$))$_x$—W$_d$—(C(R$_e$)(R$_f$))$_y$—W$_i$-E$_j$-W$_g$—(C(R$_e$)(R$_f$))$_z$—U—V;

a, b, c, d, g, i and j are each independently an integer from 0 to 3;

p, x, y and z are each independently an integer from 0 to 10;

W at each occurrence is independently —C(O)—, —C(S)—, -T-, —(C(R$_e$)(R$_f$))$_h$—, an alkyl group, an aryl group, a heterocyclic ring, an arylheterocyclic ring, or —(CH$_2$CH$_2$O)$_q$—;

E at each occurrence is independently -T-, an alkyl group, an aryl group, —(C(R$_e$)(R$_f$))$_h$—, a heterocyclic ring, an arylheterocyclic ring, or —(CH$_2$CH$_2$O)$_q$—;

T at each occurrence is independently a covalent bond, a carbonyl, an oxygen, —S(O)$_o$— or —N(R$_a$)R$_i$;

h is an integer form 1 to 10;

q is an integer from 1 to 5;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, W$_h$, —(CH$_2$)$_o$—U—V, or —(C(R$_g$)(R$_h$))$_k$—U—V, or R$_e$ and R$_f$ taken together with the carbons to which they are attached form a carbonyl, a methanthial, a heterocyclic ring, a cycloalkyl group, an aryl group, an oxime, a hydrazone or a bridged cycloalkyl group;

R$_g$ and R$_h$ at each occurrence are independently R$_e$;

k is an integer from 1 to 3;

U at each occurrence is independently a covalent bond, a carbonyl, an oxygen, —S(O)$_o$— or —N(R$_a$)R$_i$;

o is an integer from 0 to 2;

R$_a$ is a lone pair of electrons, a hydrogen or an alkyl group;

R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —CH$_2$—C(U—V)(R$_e$)(R$_f$), a bond to an adjacent atom creating a double bond to that atom, —(N$_2$O$_2$—)$^-$.M$^+$, wherein M$^+$ is an organic or inorganic cation; and with the proviso that the compounds of Formula (I) must contain at least one NO group, and/or at least one NO$_2$ group; wherein the at least one NO group and/or the at least one NO$_2$ group is linked to the compound of Formula (I) through an oxygen atom, a nitrogen atom or a sulfur atom.

In cases where R$_e$ and R$_f$ are a heterocyclic ring or taken together R$_e$ and R$_f$ are a heterocyclic ring, then R$_i$ can be a substituent on any disubstituted nitrogen contained within the radical where R$_i$ is as defined herein.

In cases where multiple designations of variables which reside in sequence are chosen as a "covalent bond" or the integer chosen is 0, the intent is to denote a single covalent bond connecting one radical to another. For example, E$_0$ would denote a covalent bond, while E$_2$ denotes (E-E) and (C(R$_e$)(R$_f$))$_2$ denotes —C(R$_e$)(R$_f$)—C(R$_e$)(R$_f$)—, where R$_e$ and R$_f$ at each occurrence are each independently selected from those moieties defined herein.

Another embodiment, the invention describes nitrosated and/or nitrosylated rapamycin compounds and pharmaceutically acceptable salts thereof, and/or stereoisomers thereof, of Formula (II);

wherein the compound of Formula (II) is:

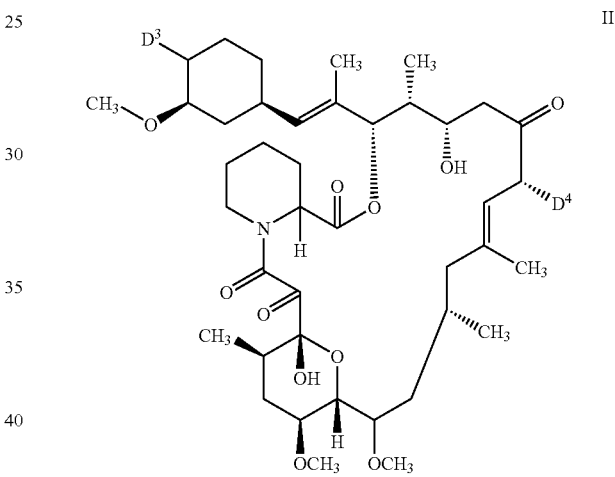

wherein:

D$^4$ is:

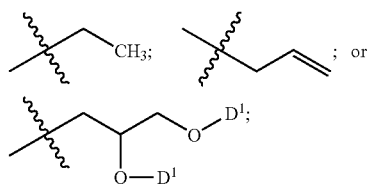

D$^1$ and D$^3$ are as defined herein; and with the proviso that the compounds of Formula (II) must contain at least one NO group, and/or at least one NO$_2$ group; wherein the at least one NO group and/or the at least one NO$_2$ group is linked to the compound of Formula (II) through an oxygen atom, a nitrogen atom or a sulfur atom.

Compounds of the invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

In preferred embodiments the compounds of Formula (I) are a nitrosated rapamycin, a nitrosylated rapamycin, a nitrosated and nitrosylated rapamycin, a nitrosated 42-deoxy-42-(1H-tetrazol-1-yl)-rapamycin, a nitrosylated 42-deoxy-42-(1H-tetrazol-1-yl)-rapamycin, a nitrosated and nitrosylated 42-deoxy-42-(1H-tetrazol-1-yl)-rapamycin, a nitrosated 42-deoxy-42-(2H-tetrazol-1-yl)-rapamycin, a nitrosylated 42-deoxy-42-(2H-tetrazol-1-yl)-rapamycin, a nitrosated and nitrosylated 42-deoxy-42-(2H-tetrazol-1-yl)-rapamycin, a nitrosated 42-O-(2-hydroxyethyl)-rapamycin, a nitrosylated 42-O-(2-hydroxyethyl)-rapamycin, a nitrosated and nitrosylated 42-O-(2-hydroxyethyl)-rapamycin and the compounds of Formula (II) are a nitrosated tacrolimus, a nitrosylated tacrolimus, a nitrosated and nitrosylated tacrolimus, a nitrosated ascomycin, a nitrosylated ascomycin, a nitrosated and nitrosylated ascomycin, and pharmaceutically acceptable salts thereof, and/or stereoisomers thereof.

The compounds of Formulas (I) and (II) can be synthesized following the methods described herein. The reactions are performed in solvents appropriate to the reagents, and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is known in the art for protecting thiol and alcohol groups against undesirable reactions during a synthetic procedure and many such protecting groups are known, e.g., T. H. Greene and P. G. M. Wuts, *Protective Groups in Organic Synthesis*, John Wiley & Sons, New York (1999), which is incorporated herein in its entirety.

Some of the compounds of the invention are synthesized as shown in Schemes 1 through 9 given below, in which $D^1$, $D^2$, $D^3$, E, K, U, V, W, $R_e$, $R_f$, $R_a$, $R_i$, $R^3$, a, b, c, d, g, h, i, j, k, o, p, q, x, y and z are as defined herein or as depicted in the reaction schemes for compounds of Formula I; $P^1$ is an oxygen protecting group, $P^2$ is a sulfur protecting group; and $A_1$, $A_2$ and $A_3$ are each independently chosen as a lower alkyl group or a phenyl group. Nitroso compounds of Formula (I) wherein $A_1$, $A_2$ and $A_3$ are as defined herein, $R^3$ is an oxygen, $D^1$ is a hydrogen or a nitroso group, $D^2$ is a methyl group, and a nitrite is representative of the $D^1$ group at position 31 as defined herein, may be prepared as shown in Scheme 1. The 42-hydroxy group of Formula 1 is converted to the trialkylsilyloxy group of Formula 2 by reaction with silyl chloride and an amine in an inert solvent. Preferred methods for the preparation of silyloxy groups are reacting the alcohol with triethylsilylchloride in the presence of pyridine in an anhydrous inert solvent, such as, dichloromethane, at 0° C., or reacting tert-butyldimethylsilylchloride in the presence of imidazole in an anhydrous inert solvent, such as, DMF, at 60° C. The compound of the Formula 2 is then converted to the compound of the Formula 3 by reaction with a suitable nitrosylating agent, such as, thionyl chloride nitrite, thionyl dinitrite, or nitrosium tetrafluoroborate, in a suitable anhydrous solvent, such as, methylene chloride, THF, DMF or acetonitrile, with or without an amine base, such as, pyridine or triethylamine. Deprotection of the 42-hydroxyl moiety (fluoride ion or mildly acidic conditions, such as, acetic acid/THF/water are the preferred methods for removing silyl ether protecting groups) produces the compound of the Formula IA.

Scheme 1

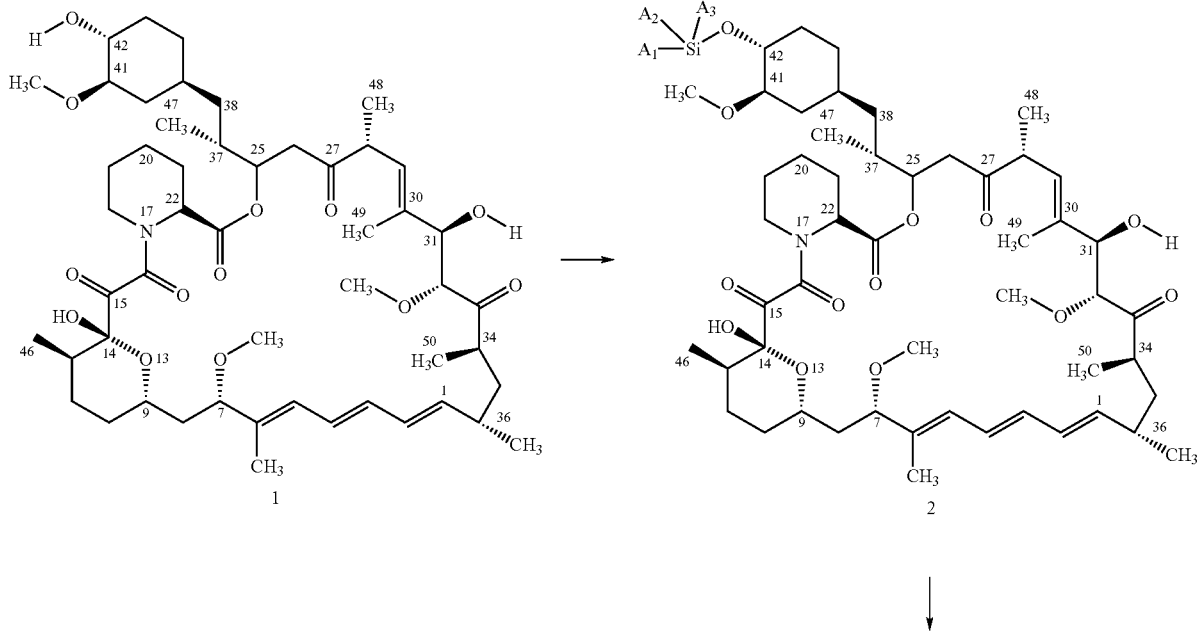

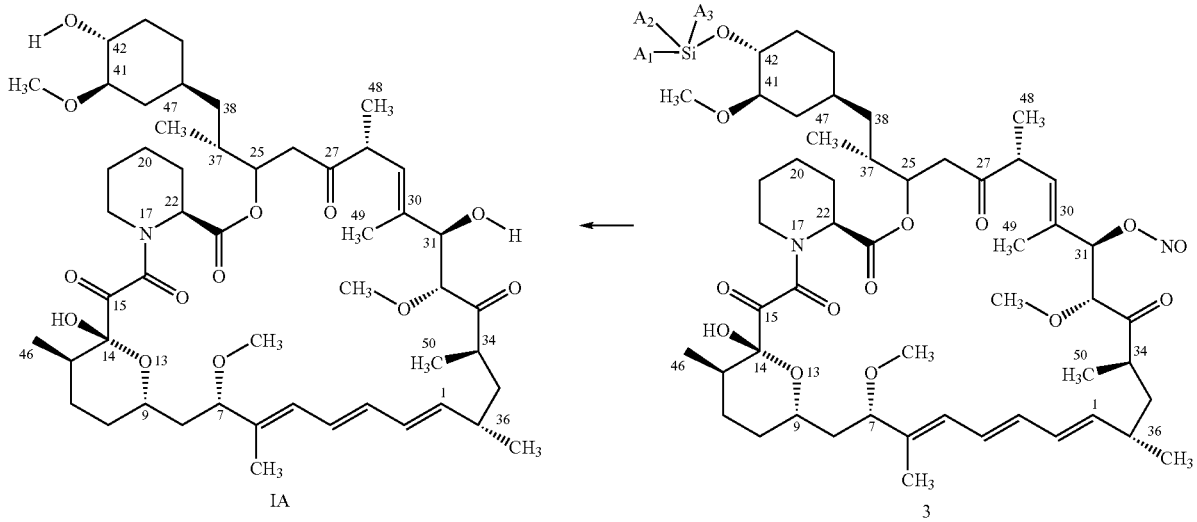

Nitroso compounds of Formula (I) wherein $A_1$, $A_2$ and $A_3$ are as defined herein, $R^3$ is an oxygen, $D^1$ is a hydrogen or a nitroso group, $D^2$ is a methyl group, and a nitrite is representative of the $D^1$ group at position 42 as defined herein, may be prepared as shown in Scheme 2. The 31-hydroxy group of Formula 1 is converted to the trialkylsilyloxy group of Formula 4 by reaction with two equivalents of silyl chloride and an amine in an inert solvent followed by removal of the silyl group from position 42. Preferred methods for the preparation of silyloxy groups are reacting the alcohols with triethylsilylchloride in the presence of pyridine in an anhydrous inert solvent, such as, dichloromethane, at 0° C., or reacting with tertbutyldimethylsilylchloride in the presence of imidazole in an anhydrous inert solvent, such as, DMF, at 60° C. Deprotection of silyl group at position 42 can be accomplished under mildly acidic conditions, such as, acetic acid/THF/water. The compound of Formula 4 is then converted to the compound of Formula 5 by reaction with a suitable nitrosylating agent, such as, thionyl chloride nitrite, thionyl dinitrite, or nitrosium tetrafluoroborate, in a suitable anhydrous solvent, such as, methylene chloride, THF, DMF or acetonitrile, with or without an amine base, such as, pyridine or triethylamine. Deprotection of the 31-hydroxyl moiety (fluoride ion or aqueous acid are the preferred methods for removing silyl ether protecting groups) produces the compound of Formula IB.

Scheme 2

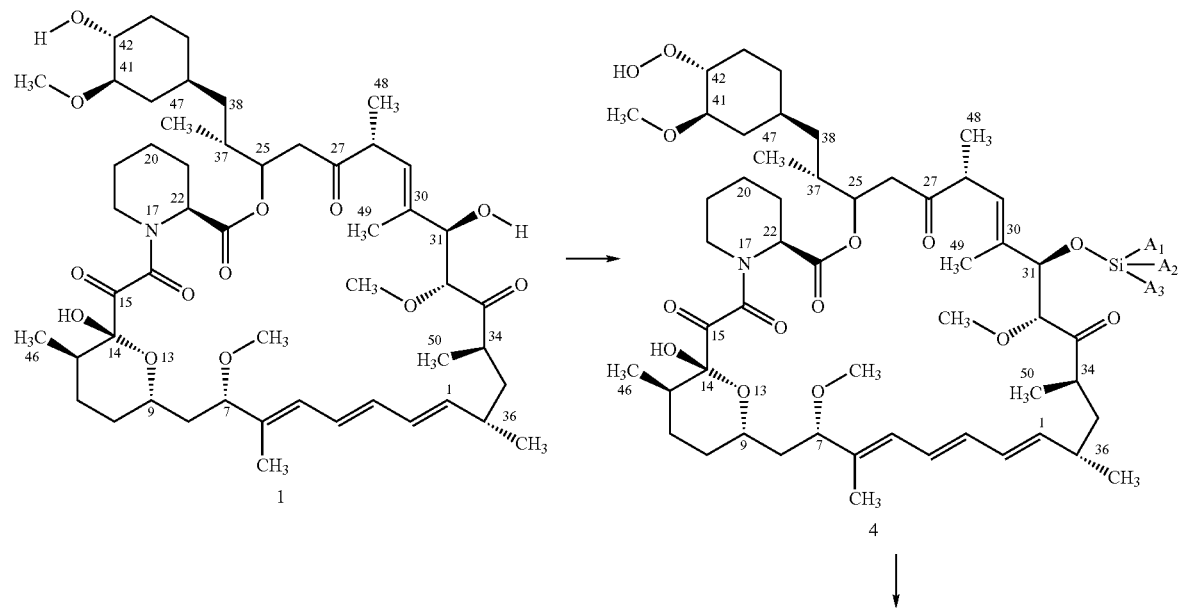

-continued

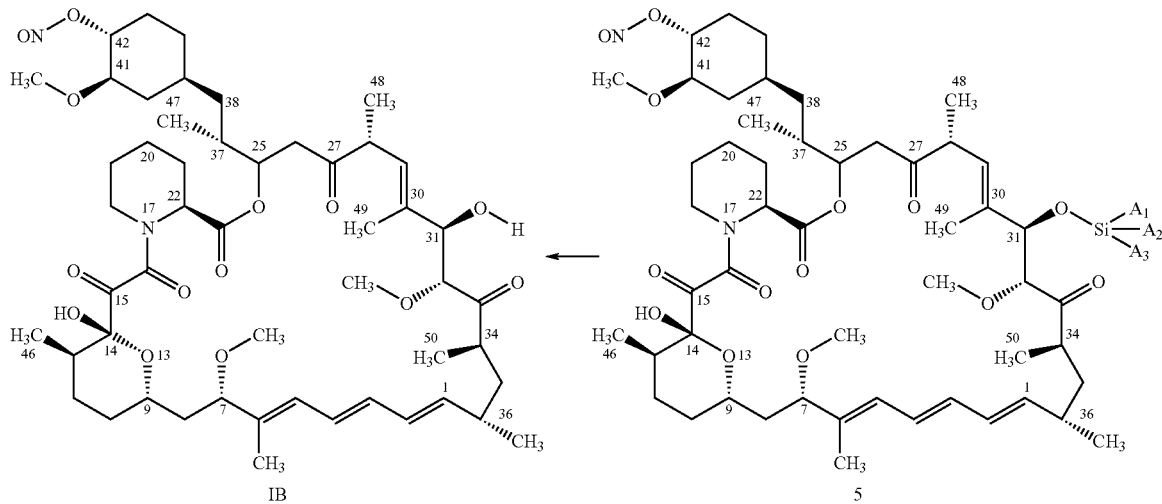

IB

5

Nitroso compounds of Formula (I) wherein $A_1$, $A_2$ and $A_3$ are as defined herein, $R^3$ is an oxygen, $D^1$ is a hydrogen or a nitroso group, $D^2$ is a methyl group, and a nitrosothiol is representative of the $D^1$ group at position 42 as defined herein, may be prepared as shown in Scheme 3. The compound of Formula 4 is converted to the compound of Formula 6 by reacting the 42-hydroxyl group with trifluoromethansulfonyl chloride in the presence of 4-dimethylaminopyridine (DMAP) in an inert solvent, such as, dichloromethane, at 0° C. to room temperature. The compound of Formula 6 is converted to the thiol of the Formula 7 by displacing the triflate group with thiourea in a hindered base, such as, 2,6,-lutidine, followed by deprotection of the thiol group with morpholine. The compound of Formula 7 is then converted to the compound of Formula IC by first reaction with a suitable nitrosylating agent, such as, thionyl chloride nitrite, thionyl dinitrite, or nitrosium tetrafluoroborate, in a suitable anhydrous solvent, such as, methylene chloride, THF, DMF or acetonitrile, with or without an amine base, such as, pyridine or triethylamine, followed by deprotection of the 31-hydroxyl moiety (fluoride ion or aqueous acid are the preferred methods for removing silyl ether protecting groups) to produce the compound of Formula IC.

Scheme 3

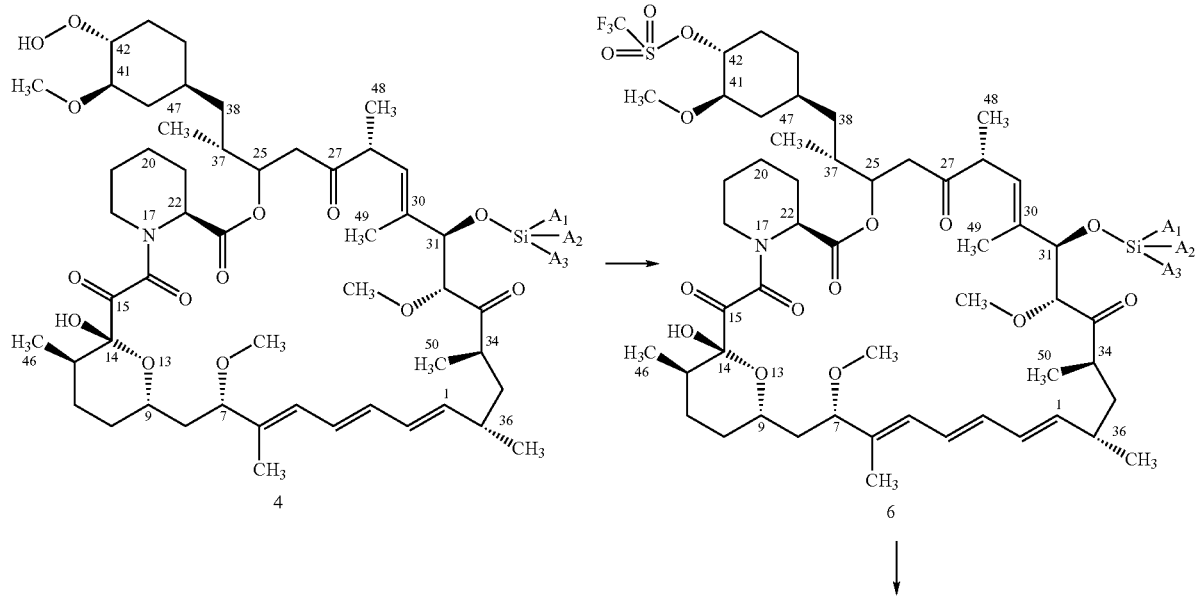

4

6

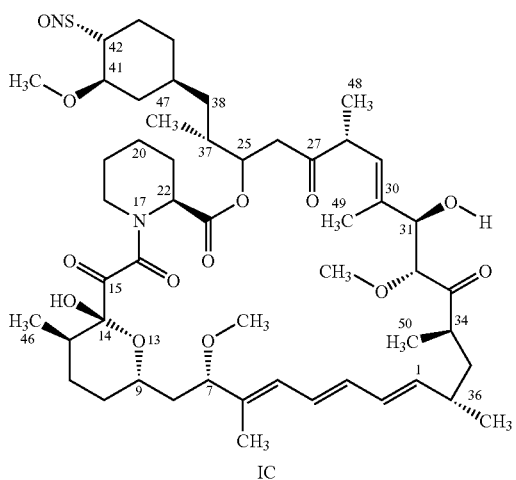

IC

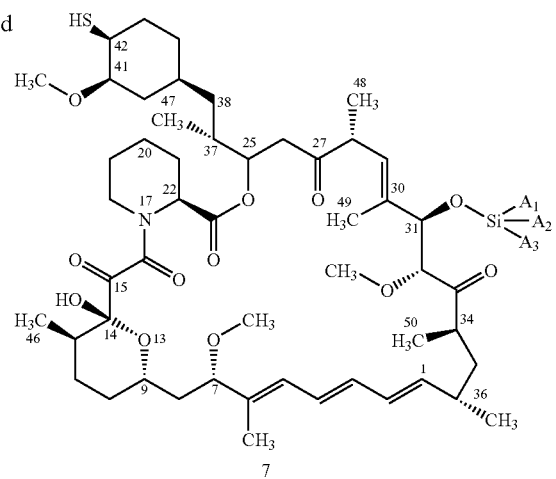

7

Nitroso compounds of Formula (I) wherein W, E, $R_e$, $R_f$, $R^3$, a, b, c, d, g, i, j, p, v, x, z, $A_1$, $A_2$ and $A_3$ are as defined herein, $R^3$ is an oxygen, $D^1$ is a hydrogen or K, $D^2$ is a methyl group, and a nitrite containing ester is representative of the $D^1$ group at position 31 as defined herein, may be prepared as outlined in Scheme 4. The 31-hydroxyl group of the compound of Formula 2 is converted to the ester of Formula 8, wherein R is $—W_{a-1}\text{-}E_b\text{-}(C(R_e)(R_f))_p\text{-}E_c\text{-}(C(R_e)(R_f))_x—W_d—(C(R_e)(R_f))_y—W_i\text{-}E_j\text{-}W_g—(C(R_e)(R_f))_z$, by reaction with an appropriate protected alcohol containing active acylating agent, wherein $P^1$ is as defined herein. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 31-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 31-hydroxyl, preferably in the presence of a condensation catalyst, such as, DMAP, and a tertiary amine base, such as, triethylamine, to produce the ester. Alternatively, the protected alcohol containing acid and 31-hydroxyl may be coupled to produce the ester by treatment with a dehydration agent, such as, dicyclohexylcarbodiimide (DCC) or 1-ethyl-3 (3-dimethylaminopropyl) carbodiimide hydrochloride (EDAC.HCl) with a catalyst, such as, DMAP or 1-hydroxybenzotriazole (HOBt). Preferred protecting groups for the alcohol moiety are as a tetrahydrofuranyl or trifluoroacetate ester. Deprotection of the hydroxyl moiety (mild aqueous acid, such as, 0.01 N HCl/THF or acetic acid/THF/water is preferred for the removal of the tetrahydrofuranyl group, while mildly acidic, neutral or mildly basic conditions, such as, THF/water, alcohol/water or acetonitrile/water are preferred for the removal of the trifluoroacetate group) followed by reaction with a suitable nitrosylating agent, such as, thionyl chloride nitrite, thionyl dinitrite, or nitrosonium tetrafluoroborate, in a suitable anhydrous solvent, such as, dichloromethane, THF, DMF, or acetonitrile with or without an amine base such as, pyridine or triethylamine, gives the compounds of Formula 9. Deprotection of the 42-hydroxyl moiety (fluoride ion or mildly acidic conditions, such as, acetic acid/THF/water are the preferred methods for removing silyl ether protecting groups) produces the compounds of Formula ID.

Scheme 4

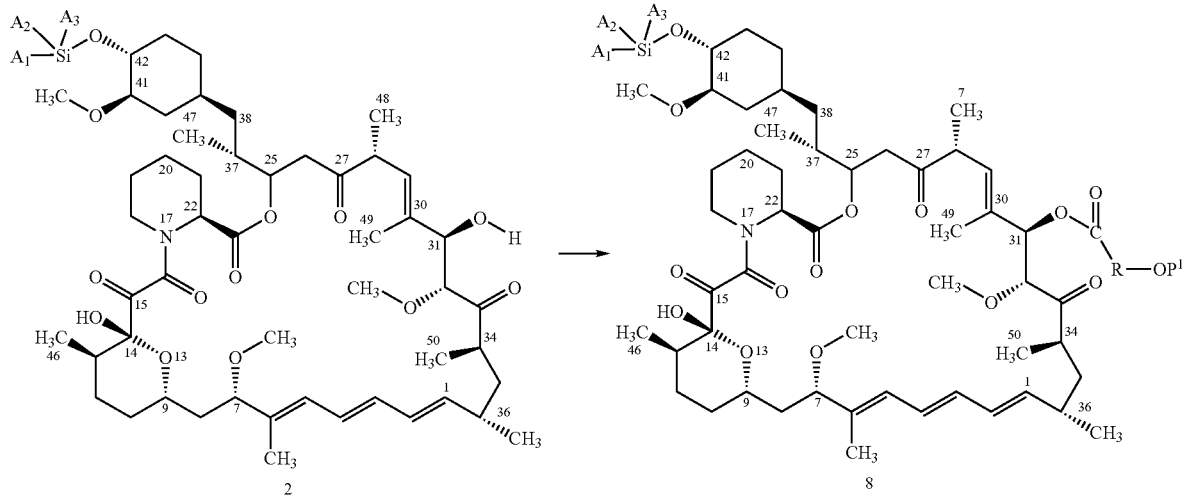

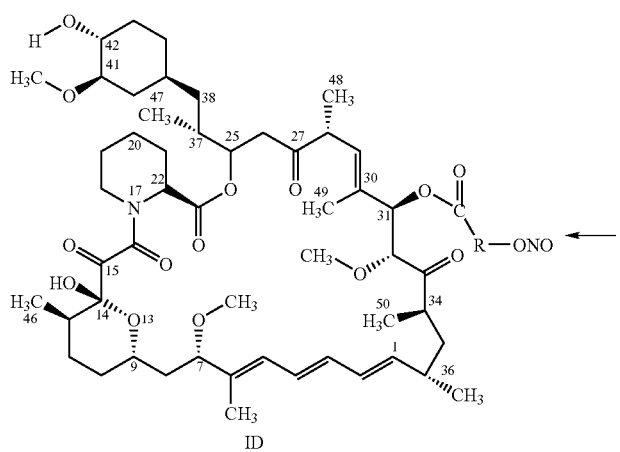

ID

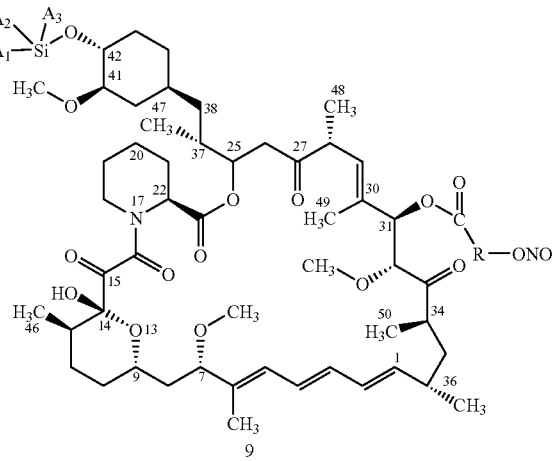

9

Nitroso compounds of Formula (I) wherein $A_1$, $A_2$ and $A_3$ are as defined herein, $R^3$ is an oxygen, $D^1$ is a hydrogen or K, $D^2$ is a methyl group, and a nitrite containing ester is representative of the $D^1$ group at position 42 as defined herein, may be prepared as outlined in Scheme 5. The 42-hydroxyl group of the compound of Formula 4 is converted to the ester of Formula 10, wherein R is as defined herein, by reaction with an appropriate protected alcohol containing active acylating agent, wherein $P^1$ is as defined herein. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 42-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 42-hydroxyl, preferably in the presence of a condensation catalyst, such as, DMAP, and a tertiary amine base, such as, triethylamine, to produce the ester. Alternatively, the protected alcohol containing acid and 42-hydroxyl may be coupled to produce the ester by treatment with a dehydration agent, such as, dicyclohexylcarbodiimide (DCC) or 1-ethyl-3 (3-dimethylaminopropyl) carbodiimide hydrochloride (EDAC.HCl) with a catalyst, such as, DMAP or 1-hydroxybenzotriazole (HOBt). Preferred protecting groups for the alcohol moiety are as a benzyl ether or a benzyl carbonate. Preferred protecting groups for the alcohol moiety are as a tetrahydrofuranyl or trifluoroacetate ester. Deprotection of the hydroxyl moiety (mild aqueous acid, such as, 0.01 N HCl/THF or acetic acid/THF/water is preferred for the removal of the tetrahydrofuranyl group, while mildly acidic, neutral or mildly basic conditions, such as, THF/water, alcohol/water or acetonitrile/water are preferred for the removal of the trifluoroacetate group) followed by reaction with a suitable nitrosylating agent, such as, thionyl chloride nitrite, thionyl dinitrite, or nitrosonium tetrafluoroborate, in a suitable anhydrous solvent, such as, dichloromethane, THF, DMF, or acetonitrile with or without an amine base such as, pyridine or triethylamine, gives the compounds of Formula 11. Deprotection of the 31-hydroxyl moiety (fluoride ion or aqueous acid are the preferred methods for removing silyl ether protecting group) produces the compounds of Formula IE.

Scheme 3

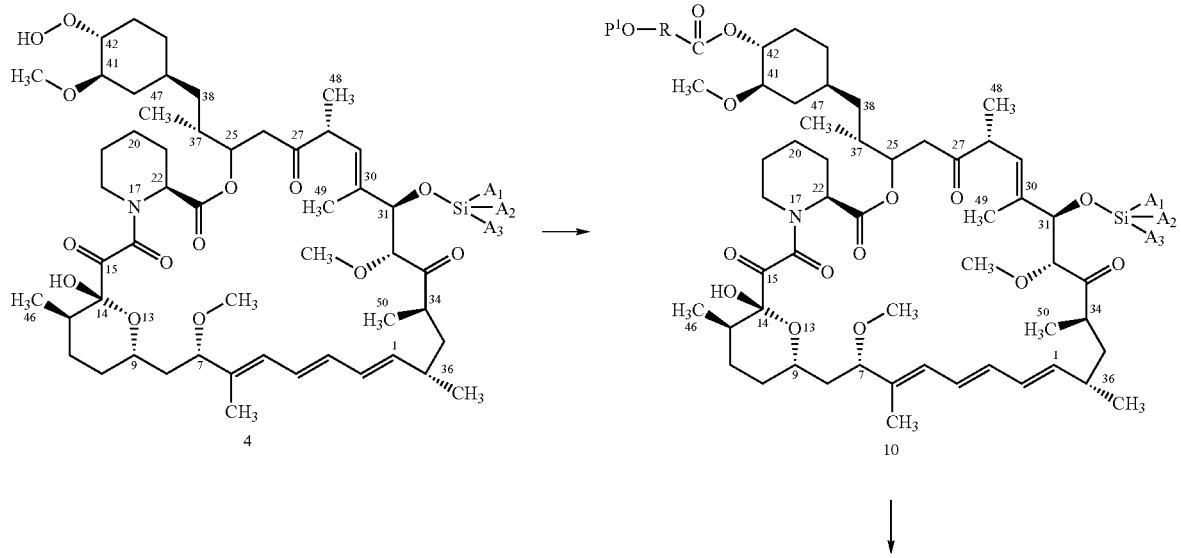

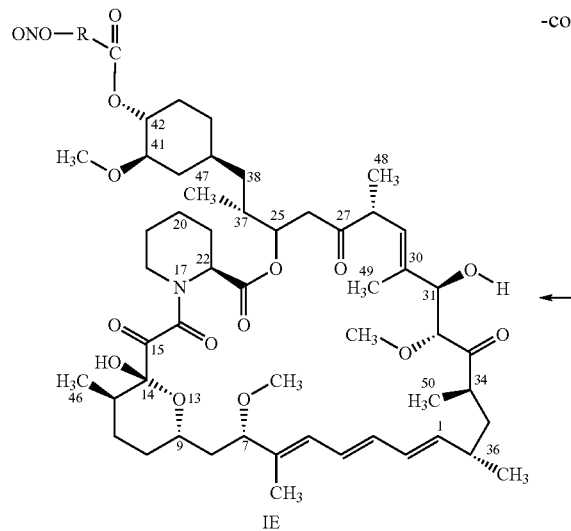

IE

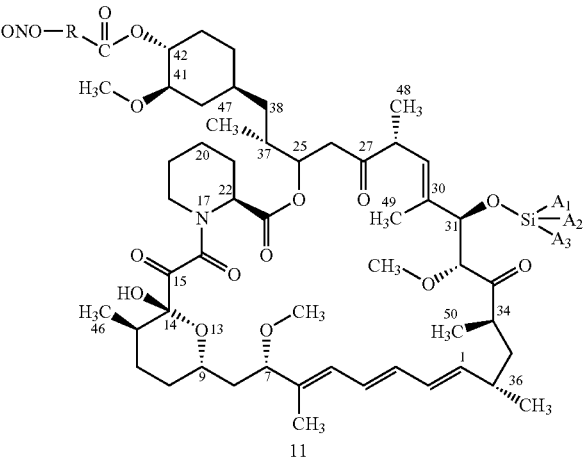

11

Nitroso compounds of Formula (I) wherein $A_1$, $A_2$ and $A_3$ are as defined herein, $R^3$ is an oxygen, $D^1$ is a hydrogen or K, $D^2$ is a methyl group, and a nitrosothiol containing ester is representative of the $D^1$ group at position 31 as defined herein, may be prepared as outlined in Scheme 6. The 31-hydroxyl group of the compound of Formula 2 is converted to the ester of Formula 12, wherein R is as defined herein, by reaction with an appropriate protected thiol containing active acylating agent, wherein $P^2$ is as defined herein. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 31-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 31-hydroxyl, preferably in the presence of a condensation catalyst, such as, DMAP, and a tertiary amine base, such as, triethylamine, to produce the ester. Alternatively, the protected thiol containing acid and the 31-hydroxyl may be coupled to produce the ester by treatment with a dehydration agent, such as, DCC or EDAC.HCl, with a catalyst, such as, DMAP or HOBt. Preferred protecting groups for the thiol moiety are as a thioester, such as, thioacetate or thiobenzoate, as a disulfide, as a thiocarbamate, such as, N-methoxymethyl thiocarbamate, or as a thioether, such as, paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters, and N-methoxymethyl thiocarbamates and mercuric trifluoroacetate, silver nitrate or strong acids, such as, trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as, a lower alkyl nitrite, such as, tert-butyl nitrite, in a suitable anhydrous solvent, such as, methylene chloride, THF, DMF or acetonitrile, produces the compound of Formula 13. Deprotection of the 42-hydroxyl moiety (fluoride ion or mildly acidic conditions, such as, acetic acid/THF/water are the preferred methods for removing silyl ether protecting groups) produces the compound of Formula IF.

Scheme 6

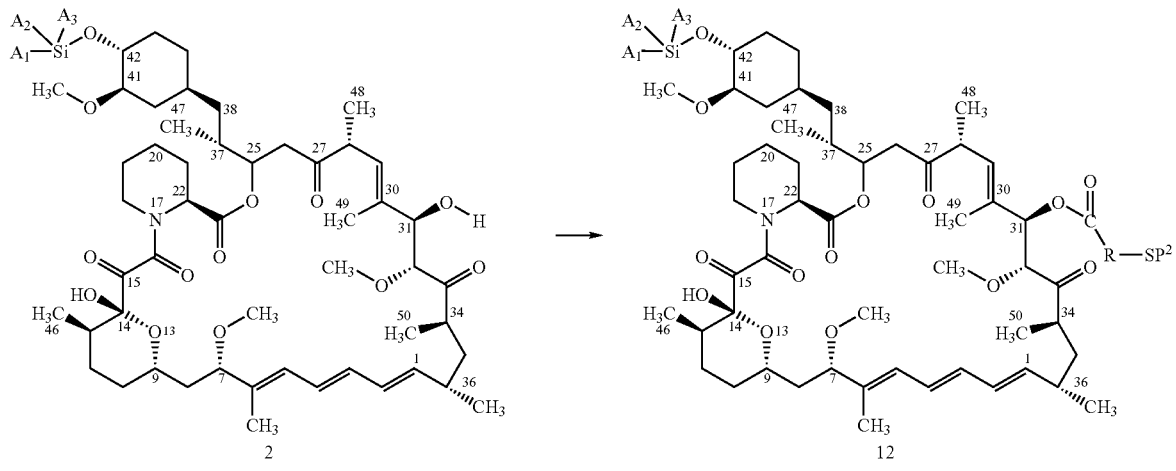

2

12

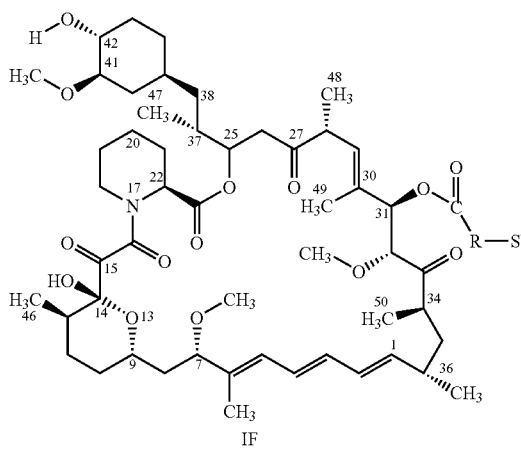

IF

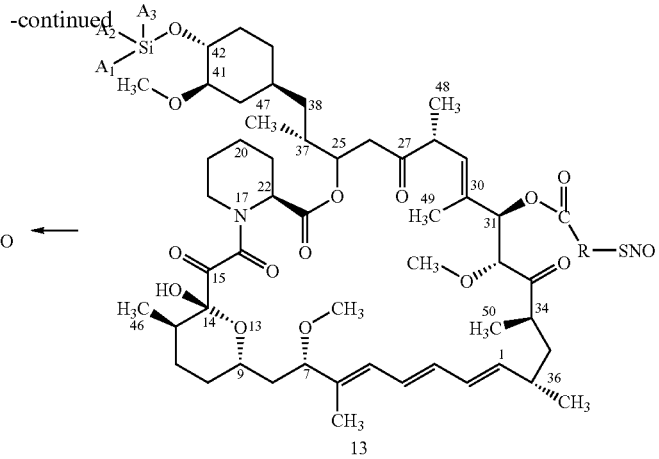

13

Nitroso compounds of Formula (I) wherein $A_1$, $A_2$ and $A_3$ are as defined herein, $R^3$ is an oxygen, $D^1$ is a hydrogen or K, $D^2$ is a methyl group, and a nitrosothiol containing ester is representative of the $D^1$ group at position 42 as defined herein, may be prepared as outlined in Scheme 7. The 42-hydroxyl group of the compound of Formula 4 is converted to the ester of Formula 14, wherein R is as defined herein, by reaction with an appropriate protected thiol containing active acylating agent, wherein $P^2$ is as defined herein. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 42-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 42-hydroxyl, preferably in the presence of a condensation catalyst, such as, DMAP, and a tertiary amine base, such as, triethylamine, to produce the ester. Alternatively, the protected thiol containing acid and the 42-hydroxyl may be coupled to produce the ester by treatment with a dehydration agent, such as, DCC or EDAC.HCl, with a catalyst, such as, DMAP or HOBt. Preferred protecting groups for the thiol moiety are as a thioester, such as, thioacetate or thiobenzoate, as a disulfide, as a thiocarbamate, such as, N-methoxymethyl thiocarbamate, or as a thioether, such as, paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters, and N-methoxymethyl thiocarbamates and mercuric trifluoroacetate, silver nitrate or strong acids such as, trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as, a lower alkyl nitrite, such as, tert-butyl nitrite, in a suitable anhydrous solvent, such as, methylene chloride, THF, DMF or acetonitrile, produces the compounds of Formula 15. Deprotection of the 31-hydroxyl moiety (fluoride ion or aqueous acid are the preferred methods for removing silyl ether protecting group) produces the compounds of Formula IG.

Scheme 7

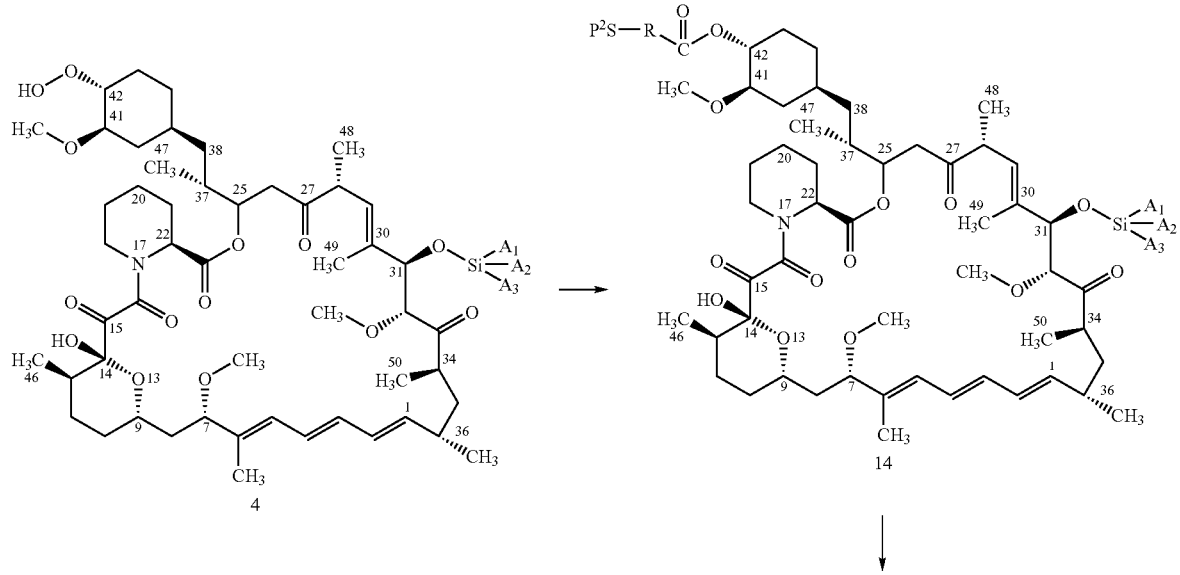

-continued

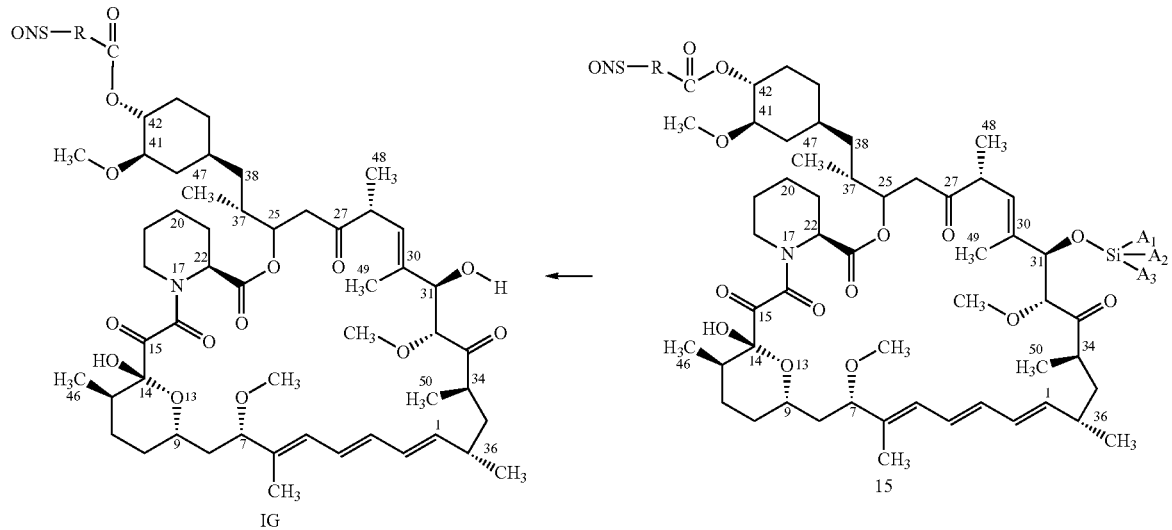

IG

Nitro compounds of Formula (I) wherein $A_1$, $A_2$, and $A_3$ are as defined herein, $R^3$ is an oxygen, $D_1$ is a hydrogen or K, $D^2$ is a methyl group, and a nitrate containing ester is representative of the $D^1$ group at position 31 as defined herein, may be prepared as outlined in Scheme 8. The 31-hydroxyl group of the compound of Formula 2 is converted to the ester of Formula 16, wherein R is as defined herein by reaction with an appropriate protected nitrate containing active acylating agent. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 31-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 31-hydroxyl, preferably in the presence of a condensation catalyst, such as, DMAP, and a tertiary amine base, such as, triethylamine, to produce the ester. Alternatively, the nitrate containing acid and 31-hydroxyl may be coupled to produce the ester by treatment with a dehydration agent, such as, DCC or EDAC.HCl, with a catalyst such as, DMAP or HOBt. Deprotection of the 42-hydroxyl moiety (fluoride ion or mildly acidic conditions, such as, acetic acid/THF/water are the preferred methods for removing silyl ether protecting groups) produces the compound of Formula IH.

Scheme 8

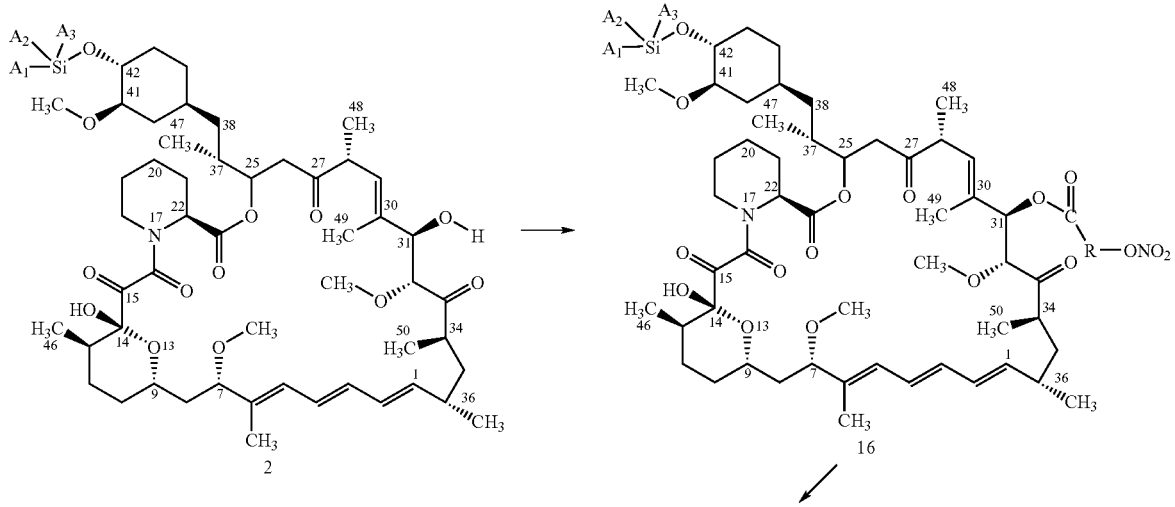

-continued

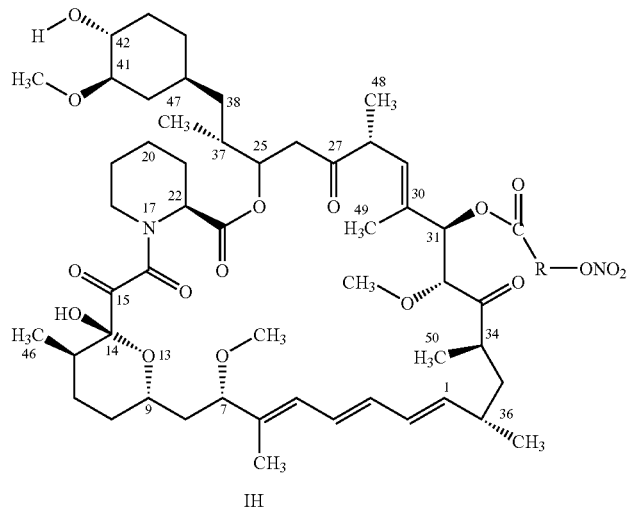

IH

Nitro compounds of Formula (I) wherein $A_1$, $A_2$ and $A_3$ are as defined herein, $R^3$ is an oxygen, $D^1$ is a hydrogen or K, $D^2$ is a methyl group, and a nitrate containing ester is representative of the $D^1$ group at position 42 as defined herein, may be prepared as outlined in Scheme 9. The 42-hydroxyl group of the compound of Formula 4 is converted to the ester of Formula 17, wherein R is as defined herein by reaction with an appropriate protected nitrate containing active acylating agent. Preferred methods for the preparation of esters are initially forming the mixed anhydride via reaction of the acid with a chloroformate, such as, isobutylchloroformate, in the presence of a non-nucleophilic base, such as, triethylamine, in an anhydrous inert solvent, such as, dichloromethane, diethylether or THF. The mixed anhydride is then reacted with the 42-hydroxyl, preferably in the presence of a condensation catalyst, such as, DMAP. Alternatively, the acid may first be converted to the acid chloride by treatment with oxalyl chloride in the presence of a catalytic amount of DMF. The acid chloride is then reacted with the 42-hydroxyl, preferably in the presence of a condensation catalyst, such as, DMAP, and a tertiary amine base, such as, triethylamine, to produce the ester. Alternatively, the nitrate containing acid and 42-hydroxyl may be coupled to produce the ester by treatment with a dehydration agent, such as, DCC or EDAC.HCl, with a catalyst such as, DMAP or HOBt. Deprotection of the 31-hydroxyl moiety (fluoride ion or aqueous acid are the preferred methods for removing silyl ether protecting group) produces the compound of Formula IJ.

Scheme 9

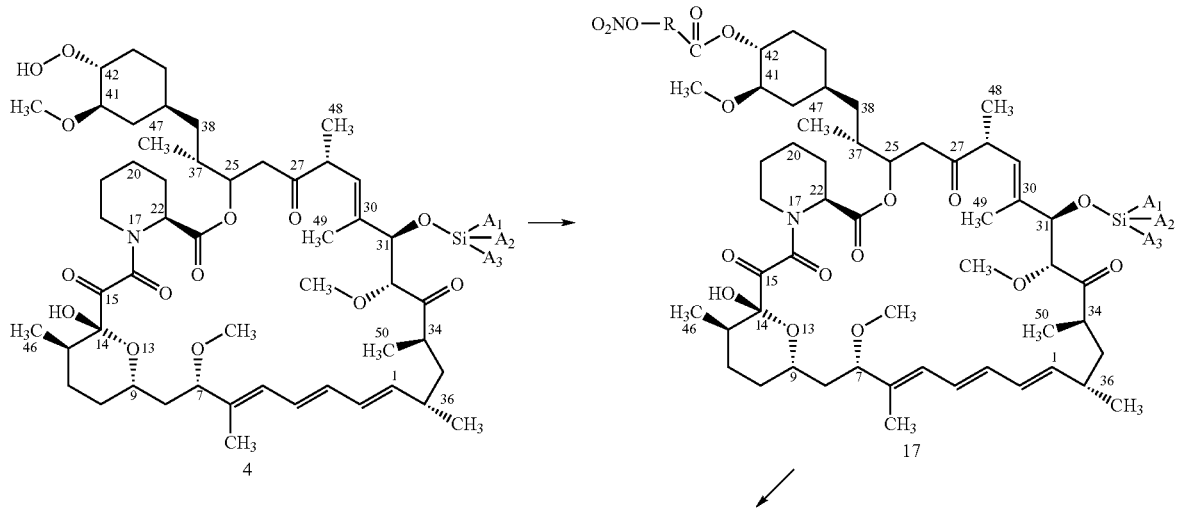

-continued

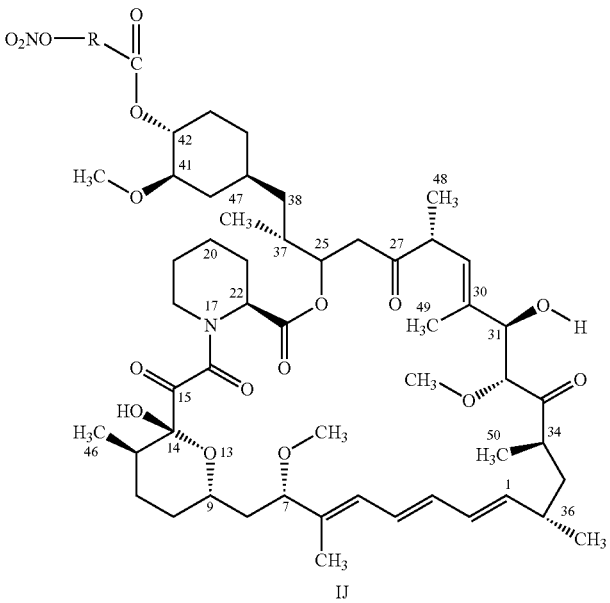

IJ

The compounds of the invention include rapamycin compounds, including those described herein, which have been nitrosated and/or nitrosylated through one or more sites such as, oxygen (hydroxyl condensation), sulfur (sulfhydryl condensation) and/or nitrogen. The nitrosated and/or nitrosylated rapamycin compounds of the invention donate, transfer or release a biologically active form of nitrogen monoxide (nitric oxide).

Nitrogen monoxide can exist in three forms: NO– (nitroxyl), NO. (nitric oxide) and NO+ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO+) does not react with $O_2$ or $O_2$— species, and functionalities capable of transferring and/or releasing NO+ and NO– are also resistant to decomposition in the presence of many redox metals. Consequently, administration of charged NO equivalents (positive and/or negative) does not result in the generation of toxic by-products or the elimination of the active NO moiety.

Compounds contemplated for use in the invention (e.g., rapamycin compounds and/or nitrosated and/or nitrosylated rapamycin compounds) are, optionally, used in combination with nitric oxide and/or compounds that release nitric oxide or otherwise directly or indirectly deliver or transfer nitric oxide to a site of its activity, such as, on a cell membrane in vivo.

The term "nitric oxide" encompasses uncharged nitric oxide (NO.) and charged nitrogen monoxide species, preferably charged nitrogen monoxide species, such as nitrosonium ion (NO+) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep.*

*Proc. Int.*, 15(3):165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; or (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an aralkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q-, or $-(C(R_g)(R_h))_k$-T-Q or $R_e$ and $R_f$ taken together are an oxo, a methanthial, a heterocyclic ring, a cycloalkyl group, an oxime, a hydrazone or a bridged cycloalkyl group; Q is $-NO$ or $-NO_2$; and T is independently a covalent bond, a carbonyl, an oxygen, $-S(O)_o-$ or $-N(R_a)R_i$, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, $-CH_2-C(T-Q)(R_g)(R_h)$, or $-(N_2O_2-)^-.M^+$, wherein $M^+$ is an organic or inorganic cation; with the proviso that when $R_i$ is $-CH_2-C(T-Q)(R_g)(R_h)$ or $-(N_2O_2-).M^+$; then "-T-Q" can be a hydrogen, an alkyl group, an alkoxyalkyl group, an aminoalkyl group, a hydroxy group or an aryl group; and $R_g$ and $R_h$ at each occurrence are independently $R_e$.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S— amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—$N(O-M^+)$—$NO$, where $R^{1'''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and/or nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, Nature, 327:524-526 (1987); Ignarro et al, Proc. Natl. Acad. Sci. USA, 84:9265-9269 (1987)).

The invention is also based on the discovery that the administration of a therapeutically effective amount of the compounds and compositions described herein is effective for treating or preventing cardiovascular diseases and disorders. For example, the patient can be administered a therapeutically effective amount of at least one nitrosated and/or nitrosylated rapamycin compound of the invention. In another embodiment, the patient can be administered a therapeutically effective amount of at least one rapamycin compound, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In yet another embodiment, the patient can be administered a therapeutically effective amount of at least one rapamycin compound, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide, or is a substrate for nitric oxide synthase. The compounds can be administered separately or in the form of a composition.

A "therapeutic agent" useful in the invention includes, but is not limited to, agents which biologically stent a vessel and/or reduce or inhibit vascular or non-vascular remodeling and/or inhibit or reduce vascular or non-vascular smooth muscle proliferation following a procedural vascular or non-vascular trauma. The "therapeutic agents" of the invention include agents that inhibit the cellular activity of a vascular or non-vascular smooth muscle cell, for example, proliferation, migration, increase in cell volume, increase in extracellular matrix synthesis (e.g., collagens, proteoglycans, and the like), or secretion of extracellular matrix materials by the cell. Suitable "therapeutic agents" useful in the invention, include, but are not limited to, antithrombogenic agents (such as, for example, heparin, covalent heparin, hirudin, hirulog, coumadin, protamine, argatroban, D-phenylalanyl-L-poly-L-arginyl chloromethyl ketone, and the like); thrombolytic agents (such as, for example, urokinase, streptokinase, tissueplasminogen activators, and the like); fibrinolytic agents; vasospasm inhibitors; potassium channel blockers; calcium channel blockers; antihypertensive agents (such as, for example, HYTRIN®, and the like); antimicrobial agents or antibiotics (such as, for example, adriamycin, and the like); platelet reducing agents; antimitotic, antiproliferative agents or microtubule inhibitors (such as, for example, colchicine, methotrexate, azathioprine, vincristine, vinblastine, cytochalasin, fluorouracil, adriamycin, mutamycin, tubercidin, epothilone A or B, discodermolide, taxol, and the like); antisecretory agents (such as, for example, retinoid, and the like); remodeling inhibitors; antisense nucleotides (such as, for example, deoxyribonucleic acid, and the like); anti-cancer agents (such as, for example, tamoxifen citrate, acivicin, bizelesin, daunorubicin, epirubicin, mitoxantrone, and the like); steroids (such as, for example, dexamethasone, dexamethasone sodium phosphate, dexamethasone acetate, and the like); non-steroidal antiinflammatory agents (NSAID); COX-2 inhibitors; anti-hyperlipidemic drugs; immunosuppressive agents (such as, for example cyclosporin, and the like); growth factor antagonists or antibodies (such as, for example, trapidal (a PDGF antagonist), angiopeptin (a growth hormone antagonist), angiogenin, and the like); dopamine agonists (such as, for example, apomorphine, bromocriptine, testosterone, cocaine, strychnine, and the like); radiotherapeutic agents (such as, for example, $^{60}$Co (5.3 year half life), $^{192}$Ir (73.8 days), $^{32}$P (14.3 days), $^{111}$In (68 hours), $^{90}$Y (64 hours), $^{99m}$Tc (6 hours), and the like); heavy metals functioning as radiopaque agents (such as, for example, iodine-containing compounds, barium-containing compounds, gold, tantalum, platinum, tungsten, and the like); biologic agents (such as, for example, peptides, proteins, enzymes, extracellular matrix components, cellular components, and the like); angiotensin converting enzyme (ACE) inhibitors; angiotensin II antagonists; endothelin antagonists; neutral endopeptidase inhibitors; renin inhibitiors; free radical scavengers, iron chelators or antioxidants (such as, for example, ascorbic acid, alpha tocopherol, superoxide dismutase, deferoxamine, 21-aminosteroid, and the like); sex hormone (such as, for example, estrogen, and the like); antipolymerases (such as, for example, AZT, and the like); antiviral agents (such as, for example, acyclovir, famciclovir, rimantadine hydrochloride, ganciclovir sodium, Norvir®, Crixivan®, and the like); photodynamic therapy agents (such as, for example, 5-aminolevulinic acid, meta-tetrahydroxyphenylchlorin, hexadecafluoro zinc phthalocyanine, tetramethyl hematoporphyrin, rhodamine 123, and the like); antibody targeted therapy agents (such as, for example, IgG2 Kappa antibodies against Pseudomonas aeruginosa exotoxin A and reactive with A431 epidermoid carcinoma cells, monoclonal antibody against the noradrenergic enzyme dopamine beta-hydroxylase conjugated to saporin, and the like); gene therapy agents; hormone replacement therapy (such as, for example, estrogens, conjugated estrogens, ethinyl estradiol, 17-beta-estradiol, estradiol, estropipate, and the like); and mixtures of two or more thereof. The rapamycin compounds, nitric oxide donors and/or therapeutic agents can be administered separately or in the form of a composition. The compounds and compositions of the invention can also be administered in combination with other medications used for the treatment of these diseases or disorders.

Suitable anticoagulants include, but are not limited to, heparin, coumarin, aspirin, protamine, warfarin, dicumarol, phenprocoumon, indan-1,3-dione, acenocoumarol, ansindione, and the like. Suitable anticoagulants are described more fully in the literature, such as, in Goodman and Gilman, The Pharmacological Basis of Therapeutics (9th Edition), McGraw-Hill, 1995, Pgs. 1341-1359; the Merck Index on CD-ROM, Twelfth Edition, Version 12:1, 1996; STN express file reg and file phar.

Suitable anti-hyperlipidemic drugs include, but are not limited to, statins or HMG-CoA reductase inhibitors, such as, for example, atorvastatin (LIPITOR®), bervastatin, cerivastatin (BAYCOL®), fluindostatin (Sandoz XU-62-320), fluvastatin, lovastatin (MEVACOR®), mevastatin, privastatin (PRAVACHOL®), rosuvastatin, simvastatin (ZOCOR®), velostatin (also known as synvinolin) and the like; gemfibrozil, cholystyramine, colestipol, nicotinic acid, bile acid sequestrants, such as, for example, cholestyramine, colesevelam, colestipol, poly(methyl-(3-trimethylaminopropyl) imino-trimethylene dihalide) and the like; probucol; fibric acid agents or fibrates, such as, for example, bezafibrate (Bezalip™), beclobrate, binifibrate, ciprofibrate, clinofibrate, clofibrate, etofibrate, fenofibrate (Lipidil™, Lipidil Micro™), gemfibrozil (Lopid™), nicofibrate, pirifibrate, ronifibrate, simfibrate, theofibrate and the like. Suitable anti-hyperlipidemic drugs are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable angiotensin II antagonists include, but are not limited to, angiotensin, candesartan, cilexetil, eprosartan, irbesartan, losartan, olmesartan, medoxomil, remikirin, riposartan, saralasin, tasosartan, telmisartan, valsartan, zolasartin, BMS 184698, 3-(2'(tetrazole-5-yl)-1,1'-biphen-4-yl) methyl-5,7-dimethyl-2-ethyl-3H-imidazo(4,5-b)pyridine, antibodies to angiotensin II, BAY106734, BIBR363, BMS184698, CGP42112A, CGP49870, CP148130, CL329167, DuP 753, E4177, E4188, EMD66397, EMD73495, EMD66684, EXP-3174, EXP 7711, EXP9954, FR1153332, GA0050, GA0056, HN65021, HOE720, HR720, KT3579, LF70156. LRB057, LRB081, LY266099, LY301875, ME3221, MK 954, PD123177, PD126055, SC51757, SC54629, SC52458, SL910102, TAK536, UP2696, U96849, UK77778, WAY126227, WK1260, WK1492, YH1498, YM 358, YM31472, and the like. Suitable angiotensin II antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable angiotensin-converting enzyme inhibitors (ACE inhibitors) include, but are not limited to, alacepril, benazepril, benazeprilat, captopril, ceronapril, cilazapril, delapril, duinapril, enalapril, enalaprilat, fosinopril, imidapril, lisinopril, moveltipril, moexipril, naphthopidil, pentopril, perindopril, quinapril, ramipril, rentipril, spirapril, temocapril, trandolapril, urapidil, zofenopril, acylmercapto and mercaptoalkanoyl pralines, carboxyalkyl dipeptides, carboxyalkyl dipeptide, phosphinylalkanoyl pralines, and the like. Suitable ACE inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable calcium channel blockers include, but are not limited to, amlodipine, aranidipine, barnidipine, benidipine, bepridil, cilnidipine, cinnarizine, clentiazem, diltiazen, dotarizine, efonidipine, elgodipine, fantofarone, felodipine, flunarizine, fluspirilene, gallopamil, isradipine, lacidipine, lercanidipine, lomerizine, manidipine, mibefradil, monatepil, nicardipine, nifedipine, nilvadipine, nimodipine, nisoldipine, nitrendipine, semotiadil, veraparmil, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable endothelin antagonists include, but are not limited to, bosentan, endothelin, sulfonamide endothelin antagonists, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable neutral endopeptidase inhibitors include, but are not limited to, atrial natriuretic peptides, diazapins, azepinones, ecadotril, omapatrilat, sampatrilat, BMS 189,921, and the like. Neutral endopeptidase inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and on STN Express, file phar and file registry; and in U.S. Pat. Nos. 6,057,347 and 6,297,260 assigned to NitroMed Inc., the disclosures of which are incorporated herein by reference in their entirety.

Suitable potassium channel blockers include but are not limited to, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d)(2)-benzazepine, Ribi, CPG-11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam, brotizolam, and the like. Suitable potassium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable platelet reducing agents include but are not limited to, fibrinolytic agents such as for example, ancrod, anistreplase, bisobrin lactate, brinolase, Hageman factor (i.e. factor XII) fragments, molsidomine, plasminogen activators such as, for example, streptokinase, tissue plasminogen activators (TPA), urokinase, pro-Urokinase, recombinant TPA, plasmin, plasminogen, and the like; anti-coagulant agents including but are not limited to, inhibitors of factor Xa, factor TFPI, factor VIIa, factor IXc, factor Va, factor VIIIa, inhibitors of other coagulation factors, and the like; vitamin K antagonists, such as, for example, coumarin, coumarin derivatives (e.g., warfarin sodium); glycosoaminoglycans such as, for example, heparins both in unfractionated form and in low molecular weight form; ardeparin sodium, bivalirudin, bromindione, coumarin, dalteparin sodium, danaparoid sodium; dazoxiben hydrochloride, desirudin, dicumarol, efegatran sulfate, enoxaparin sodium, ifetroban, ifetroban sodium, lyapolate sodium, nafamostat mesylate, phenprocoumon, sulfatide, tinzaparin sodium, retaplase; trifenagrel, warfarin, dextrans and the like; acadesine, anipamil, argatroban, aspirin, clopidogrel, diadenosine 5',5'''-P1,P4-tetraphosphate (Ap4A) analogs, difibrotide, dilazep dihydrochloride, dipyridamole, dopamine, 3-methoxytyramine, glucagon, glycoprotein IIb/IIIa antagonists, such as, for example, Ro-43-8857, L-700,462, iloprost, isocarbacyclin methyl ester, itazigrel, ketanserin, BM-13.177, lamifiban, lifarizine, molsidomine, nifedipine, oxagrelate, prostaglandins, platelet activating factor antagonists such as, for example, lexipafant, prostacyclins, pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612, ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as, for example, picotamide, sulotroban, ticlopidine, tirofiban, trapidil, ticlopidine, trifenagrel, trilinolein, 3-substituted 5,6-bis(4-methoxyphenyl)-1,2,4-triazines; antibodies to glycoprotein IIb/IIIa; anti-serotonin drugs, such as, for example, clopridogrel; sulfinpyrazone and the like; aspirin; dipyridamole; clofibrate; pyridinol carbamate; glucagon; caffeine; theophyllin pentoxifyllin; ticlopidine, and the like. Suitable platelet reducing agents are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable renin inhibitors include, but are not limited to, aldosterone, enalkrein, medullipin, tonin, RO 42-5892, A 65317, CP 80794, ES 1005, ES 8891, SQ 34017, urea derivatives of peptides, amino acids connected by nonpeptide bonds, di- and tri-peptide derivatives, amino acids and derivatives thereof, diol sulfonamides and sulfinyls, modified peptides, peptidyl beta-aminoacyl aminodiol carbamates, monoclonal antibodies to rennin, and the like. Suitable renin inhibitors are described more fully in U.S. Pat. Nos. 5,116,835, 5,114,937, 5,106,835, 5,104,869, 5,095,119, 5,098,924), 5,095,006, 5,089,471, 5,075,451, 5,066,643, 5,063,208, 4,845,079, 5,055,466, 4,980,283, 4,885,292), 4,780,401, 5,071,837, 5,064,965, 5,063,207, 5,036,054, 5,036,053, 5,034,512, and 4,894,437, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable COX-2 inhibitors include, but are not limited to, NS-386, nimesulide, flosulide, celecoxib, rofecoxib, COX-189, etoracoxib, valdecoxib, Bextra, Dynastat, Arcoxia, SC-57666, DuP 697, GW-406381, SC-58125, SC-58635, and the like, and mixtures of two or more thereof. Suitable COX-2 inhibitors are in U.S. Pat. Nos. 5,344,991, 5,380, 738, 5,393,790, 5,409,944, 5,434,178, 5,436,265, 5,466,823, 5,474,995, 5,510,368, 5,536,752, 5,550,142, 5,552,422, 5,604,253, 5,604,260, and 5,639,780 and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Another embodiment of the invention provides compositions comprising at least one rapamycin compound that is optionally nitrosated and/or nitrosylated, and, optionally, at least one compound that donates, transfers or releases nitric oxide and/or stimulates the endogenous production of NO or EDRF in vivo and/or is a substrate for nitric oxide synthase and/or at least one therapeutic agent, bound to a matrix. Preferably, the nitrosated and/or nitrosylated rapamycin compounds are the compounds of Formulas (I) and (II). Preferably, the compound that donates, transfers or releases nitric oxide and/or stimulates the endogenous production of NO or EDRF in vivo and/or is a substrate for nitric oxide synthase (i.e., NO donors) and the therapeutic agents are those described herein.

The rapamycin compound that is optionally nitrosated and/or nitrosylated, and, optionally, NO donors and/or therapeutic agents, can be incorporated into a natural or synthetic matrix which can then be applied with specificity to a biological site of interest. Accordingly the rapamycin compound that is optionally nitrosated and/or nitrosylated, optionally, NO donor and/or therapeutic agent is "bound to the matrix" which means that the rapamycin compound that is optionally nitrosated and/or nitrosylated, and, optionally, NO donors and/or therapeutic agent, are physically and/or chemically associated with part of, incorporated with, attached to, or contained within the natural or synthetic matrix. In one embodiment, physical association or bonding can be achieved, for example, by coprecipitation of the rapamycin compound that is optionally nitrosated and/or nitrosylated, and, optionally, NO donor and/or therapeutic agent, with the matrix. In another embodiment, chemical association or bonding can be achieved by, for example, covalent bonding of a nucleophillic moiety of the rapamycin compound that is optionally nitrosated and/or nitrosylated, and, optionally, NO donor, and/or therapeutic agent, to the matrix, such that the rapamycin compound that is optionally nitrosated and/or nitrosylated, is part of the matrix itself. In yet another embodiment, the rapamycin compound that is optionally nitrosated and/or nitrosylated, and, optionally, NO donor, and/or therapeutic agent can be incorporated into a porous layer of the matrix or into pores included in the natural or synthetic matrix. The manner in which the rapamycin compound that is optionally nitrosated and/or nitrosylated, and, optionally, NO donor and/or therapeutic agent, is associated, part of, attached to, incorporated with or contained within (i.e. "bound to") the matrix is inconsequential to the invention and all means of association, incorporation, attachment, and bonding are contemplated herein. Incorporation of the rapamycin compound that is optionally nitrosated and/or nitrosylated, and, optionally, NO donors, and/or therapeutic agents, into the matrix results in site-specific application, thereby enhancing selectivity of action for the released nitric oxide and the rapamycin compound. Additionally, incorporation of the rapamycin compound that is optionally nitrosated and/or nitrosylated, into the matrix reduces the rate of release of the nitric oxide and the rapamycin compound. This prolongs the release of the nitric oxide and the rapamycin compound thereby allowing for efficient dosing to achieve a desired biological effect so that the frequency of dosing can be reduced.

Any of a wide variety of natural or synthetic polymers can be used as the matrix in the context of the invention. It is only necessary for the matrix to be biologically acceptable. Exemplary matrixes suitable for use in the invention are polymers including, for example, polyolefins (such as, polystyrene, polyalkylenes, polypropylene, polyethylene, high molecular weight polyethylene, polyethylene oxides, high density polyethylene, polytetrafluoroethylene, polyvinylidene diflouride and polyvinylchloride), polyethylenimine or derivatives thereof, polyethers (such as, polyethylene glycol), polyesters (such as, poly-L-lactic acid, poly-D, L-lactic, poly-D-lactic, polyglycolic acid, poly-(lactide/glycolide, polyethylene terephthalate), polyether sulfones, polyanhydrides, polyhydroxybutyrates, polyamides (such as, nylon), polyurethanes, polyurethane copolymers (such as, pellethane polymers), polyacrylates (such as, polymethacrylate, poly (2-(methacryloyloxyethyl)-2'-(trimethylammonium) ethyl phosphate inner salt-co-n-dodecyl methacrylate, methylmethacrylate), polyvinylpyrrolidones, cross-linked polyvinylpyrrolidones, polyvinyl alcohols, polyvinyl acetates, halogenated polyalkylenes, polyvinyl ethers, polyvinyl aromatics, polyurethanes, polyorthoesters, polycarbonates, polyalkylenes, polycarboxylic acids (such as, for example polyacrylic acids), polycaprolactone, polyhydroxybutyrate valerate, silicones, siloxane polymers, hyaluronic acid, mixtures of polymers (such as, polylactic acid/polylysine copolymers, polyalkylene/styrene copolymers, polyurethane/polyester copolymers, polyurethane/polyether copolymers, polyethylene oxide/polypropylene oxides, ethylene-vinyl acetate copolymers, nylon/polyether copolymers, such as, vestamid), biopolymers (such as, peptides, polypeptides, proteins, chitosan, chitosan derivatives, gelatin, oligonucleotides, antibodies, peptide hormones, glycoproteins, glycogen and nucleic acids, fibrin, collagen), glycosaminoglycans, polysaccharides (such as, for example, cellulose, starches, dextrans, alginates, derivatives such as, cellulose acetate, cellulose nitrate), starburst dendrimers, natural fibrous matrix (such as, filter paper), synthetic fibrous matrix materials (such as, three-dimensional lattice of synthetic polymers and copolymers) and the like. Exemplary polymers are described in U.S. Pat. Nos. 5,705,583, 5,770,645, 5,994,444, 6,087,479 and 6,153,252, the disclosures of each of which are incorporated by reference herein in their entirety. In preferred embodiments the matrix materials are polylactic acid, polyurethane and polyalkene polymers. In another embodiment the matrix material is nitrosated and/or nitrosyalted.

The physical and structural characteristics of the matrixes suitable for use in the invention are not critical, but depend on the application. It will be appreciated by one skilled in the art that where the matrix-rapamycin compound, that is optionally nitrosated and/or nitrosylated, composition of the invention is intended for local, relatively short term administration or similar administration they need not be biodegradable. For some uses, such as, postangioplasty, coronary bypass surgery or intimal hyperplasia associated with vascular or non-vascular graft implants or the like, it may be desirable for the matrix to slowly dissolve in a physiological environment or to be biodegradable.

The nitrosated and/or nitrosylated rapamycin compound or rapamycin compound and, optionally, the compound that donates, transfers or releases nitric oxide and/or stimulates the endogenous production of NO or EDRF in vivo and/or is a substrate for nitric oxide synthase and/or therapeutic agent bound to the matrix may be administered in a wide variety of forms or delivery means. Any delivery means should adequately protect the integrity of the nitric oxide prior to its release and should control the release of the nitric oxide at such a rate, in such an amount, and in such a location as to serve as an effective means for prevention and/or treatment of cardiovascular diseases and disorders, including restenosis. Delivery means for local administration include, but are not limited to, those described herein. Delivery means for systemic administration include, for example, solutions, suspensions, emulsions, capsules, powders, sachets, tablets, effervescent tablets, topical patches, lozenges, aerosols, liposomes, microparticles, microspheres, beads and the like. The matrix itself may be structurally sufficient to serve as a delivery means.

The nitrosated and/or nitrosylated rapamycin compound or rapamycin compound and, optionally, the compound that donates, transfers or releases nitric oxide and/or stimulates the endogenous production of NO or EDRF in vivo and/or is a substrate for nitric oxide synthase and/or therapeutic agent, bound to the matrix can also be used to coat all or a portion of the surface of a medical device that comes into contact with blood (including blood components and blood products), vascular or non-vascular tissue thereby rendering the surface passive. Alternatively the rapamycin compound that is optionally nitrosated and/or nitrosylated, and the compound that donates, transfers or releases nitric oxide and/or stimulates the endogenous production of NO or EDRF in vivo and/or is a substrate for nitric oxide synthase and, optionally, the therapeutic agent, bound to the matrix can also be used to coat all or a portion of the surface of a medical device that comes into contact with blood (including blood components and blood products), vascular or non-vascular tissue thereby rendering the surface passive. U.S. Pat. Nos. 5,665,077, 5,797,887, 5,824,049 and 5,837,008, the disclosures of each of which are incorporated by reference herein in their entirety, describe methods for coating all or a portion of a surface of a medical device. Thus, for example, (i) all or a portion of the medical device may be coated with the rapamycin compound that is optionally nitrosated and/or nitrosylated, and, optionally, NO donors and/or therapeutic agents, either as the coating per se or bound to a matrix, as described herein; or (ii) all or a portion of the medical device may be produced from a material which includes the rapamycin compound that is optionally nitrosated and/or nitrosylated, and, optionally, NO donor and/or therapeutic agent, per se or bound to a matrix, as described herein.

It is also contemplated that artificial surfaces will vary depending on the nature of the surface, and such characteristics including contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of adduct, length of treatment, temperature, diluents, and storage conditions, in order to provide optimal coating of each particular type of surface.

After the medical device or artificial material has been coated with the nitrosated and/or nitrosylated rapamycin compound and, optionally, NO donor and/or therapeutic agent, or with the rapamycin compound and NO donor, and, optionally, the therapeutic agent, it will be suitable for its intended use, including, for example, implantation as a heart valve, insertion as a catheter, insertion as a stent, or for cardiopulmonary oxygenation or hemodialysis.

In another embodiment, the rapamycin compound that is optionally nitrosated and/or nitrosylated, and, optionally, NO donor, and/or therapeutic agent can be directly incorporated into the pores or reservoirs of the medical device (i.e. without a matrix or polymer). A coating of a biocompatible polymer/material could be applied over the medical device which would control the diffusion of the rapamycin compound that is optionally nitrosated and/or nitrosylated, and, optionally, NO donor, and/or therapeutic agent from the pores or reservoirs of the medical device. The manner in which the rapamycin compound that is optionally nitrosated and/or nitrosylated, and, optionally, NO donor and/or therapeutic agent, is associated, part of, attached to, incorporated with or contained within (i.e. "bound to") the medical device is inconsequential to the invention and all means of association, incorporation, attachment, and bonding are contemplated herein. Incorporation of the rapamycin compound that is optionally nitrosated and/or nitrosylated, and, optionally, NO donors, and/or therapeutic agents, into the pores or reservoirs of the medical device results in site-specific application, thereby enhancing selectivity of action for the released nitric oxide and rapamycin compound. Additionally, incorporation of the rapamycin compound that is optionally nitrosated and/or nitrosylated, into the pores or reservoirs of the medical device reduces the rate of release of the nitric oxide and the rapamycin compound. This prolongs the release of the nitric oxide and the rapamycin compound thereby allowing for efficient dosing to achieve a desired biological effect so that the frequency of dosing can be reduced. Methods for the incorporation of rapamycin into the pores or reservoirs of medical devices are disclosed in U.S. Pat. No. 6,273,913 and in EP 0 950 386 A2 and in WO 01/87372, the disclosures of each of which are incorporated by reference herein in their entirety.

The invention also describes methods for the administration of a therapeutically effective amount of the compounds and compositions described herein for treating or preventing cardiovascular diseases and disorders including, for example, restenosis and atherosclerosis. For example, the patient can be administered a therapeutically effective amount of at least one nitrosated and/or nitrosylated rapamycin compound of the invention. In another embodiment, the patient can be administered a therapeutically effective amount of at least one rapamycin compound, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In yet another embodiment, the patient can be administered a therapeutically effective amount of at least one rapamycin compound, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide, or is a substrate for nitric oxide synthase. The compounds can be administered separately or in the form of a composition.

Another embodiment of the invention provides methods for the prevention of platelet aggregation and platelet adhesion caused by the exposure of blood (including blood components or blood products) to a medical device by incorporating at least one nitrosated and/or nitrosylated rapamycin compound or rapamycin compound, and, optionally, at least one compound that donates, transfers or releases nitric oxide and/or stimulates the endogenous production of NO or EDRF in vivo and/or is a substrate for nitric oxide synthase, and/or therapeutic agent, capable of releasing a therapeutically effective amount of nitric oxide, into and/or on the portion(s) of the medical device that come into contact with blood (including blood components or blood products), vascular or non-vascular tissue. The rapamycin compound that is optionally nitrosated and/or nitrosylated, and, optionally, NO donors, may be directly or indirectly linked to the natural or synthetic polymeric material from which all or a portion of the device is made, as disclosed in U.S. Pat. No. 6,087,479, assigned to NitroMed, the disclosure of which is incorporated by reference herein in its entirety. Alternatively, the rapamycin compound that is optionally nitrosated and/or nitrosylated, and, optionally, NO donors, may be incorporated into the body of the device which is formed of a biodegradable or bioresorbable material, including the matrix described herein. Thus the nitric oxide is released over a sustained period of the resorption or degradation of the body of the device.

Another embodiment of the invention provides methods to prevent or treat pathological conditions resulting from abnormal cell proliferation, transplant rejections, autoimmune, inflammatory, proliferative, hyperproliferative or vascular diseases, to reduce scar tissue and to inhibit wound contraction by administering to a patient in need thereof a therapeutically effective amount of the compounds and/or compositions described herein. For example, the patient can be administered a therapeutically effective amount of at least one nitrosated and/or nitrosylated rapamycin compound of the invention. In another embodiment, the patient can be administered a therapeutically effective amount of at least one rapamycin compound, optionally substituted with at least one NO and/or $NO_2$ group, and at least one compound that donates, transfers or releases nitric oxide as a charged species, or elevates levels of endogenous EDRF or nitric oxide or is a substrate for nitric oxide synthase. In yet another embodiment, the patient can be administered a therapeutically effective amount of at least one rapamycin compound, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide or is a substrate for nitric oxide synthase. The rapamycin compound optionally substituted with at least one NO and/or $NO_2$ group, nitric oxide donors and/or therapeutic agents can be administered separately or in the form of a composition. The compounds and compositions of the invention can also be administered in combination with other medications used for the treatment of these disorders.

Another embodiment of the invention relates to systemic and/or local administration of the nitrosated and/or nitrosylated rapamycin compound and/or rapamycin compound, and, optionally, at least one compound that donates, transfers or releases nitric oxide and/or stimulates the endogenous production of NO or EDRF in vivo and/or is a substrate for nitric oxide synthase, to the site of injured or damaged tissue (e.g., damaged blood vessels) for the treatment of the injured or damaged tissue. Such damage may result from the use of a medical device in an invasive procedure. Thus, for example, in treating blocked vasculature by, for example, angioplasty, damage can result to the blood vessel. Such damage may be treated by use of the compounds and compositions described herein. In addition to repair of the damaged tissue, such treatment can also be used to prevent and/or alleviate and/or delay re-occlusions, for example, restenosis. The compounds and compositions can be locally delivered using any of the methods known to one skilled in the art, including but not limited to, a drug delivery catheter, an infusion catheter, a drug delivery guidewire, an implantable medical device, and the like. In one embodiment, all or most of the damaged area is coated with the nitrosated and/or nitrosylated rapamycin compound described herein per se or in a pharmaceutically acceptable carrier or excipient which serves as a coating matrix, including the matrix described herein. This coating matrix can be of a liquid, gel or semisolid consistency. The nitrosated and/or nitrosylated rapamycin compound can be applied in combination with one or more therapeutic agents, such as, those listed above. The carrier or matrix can be made of or include agents which provide for metered or sustained release of the therapeutic agents.

In preventing and/or treating cardiovascular diseases and disorders, the nitrosated and/or nitrosylated rapamycin compound and, optionally, at least one compound that donates, transfers or releases nitric oxide and/or stimulates the endogenous production of NO or EDRF in vivo and/or is a substrate for nitric oxide synthase can be administered directly to the damaged vascular or non-vascular surface intravenously by using an intraarterial or intravenous catheter, suitable for delivery of the compounds to the desired location. The location of damaged arterial surfaces is determined by conventional diagnostic methods, such as, X-ray angiography, performed using routine and well-known methods available to one skilled in the art. In addition, administration of the nitrosated and/or nitrosylated rapamycin compounds, and, optionally, NO donors, using an intraarterial or intravenous catheter is performed using routine methods well known to one skilled in the art. Typically, the compound or composition is delivered to the site of angioplasty through the same catheter used for the primary procedure, usually introduced to the carotid or coronary artery at the time of angioplasty balloon inflation. The nitrosated and/or nitrosylated rapamycin compounds, and, optionally, NO donors, slowly decompose at body temperature over a prolonged period of time releasing nitric oxide at a rate effective to prevent and/or treat cardiovascular diseases and disorders including, for example, restenosis.

When administered in vivo, the compounds and compositions of the invention can be administered in combination with pharmaceutically acceptable carriers and in dosages described herein. When the compounds and compositions of the invention are administered as a mixture of at least one nitrosated and/or nitrosylated rapamycin compound or at least one rapamycin compound and at least one nitric oxide donor, they can also be used in combination with one or more additional compounds which are known to be effective against the specific disease state targeted for treatment (e.g., therapeutic agents). The nitric oxide donors and/or therapeutic agents can be administered simultaneously with, subsequently to, or prior to administration of the rapamycin compound, including those that are substituted with one or more NO and/or $NO_2$ groups, and/or other additional compounds.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrastemal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as, transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, pastes, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as, one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as, sucrose, lactose or starch. Such dosage forms can also comprise, as in normal practice, additional substances other than inert diluents, e.g., lubricating agents such as, magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as, lactose, saccharose, sorbitol, mannitol, potato starch, corn starch, amylopectin, cellulose derivatives of gelatin. Tablets and pills can be prepared with enteric coatings. Oral formulations containing rapamycin compounds are disclosed in U.S. Pat. Nos. 5,559,121, 5,536,729, 5,989,591 and 5,985,325, the disclosures of each of which are incorporated by reference herein in their entirety.

Liquid dosage forms for oral administration can include pharmaceutically acceptable emulsions, solutions, suspensions, syrups, and elixirs containing inert diluents commonly used in the art, such as, water. Such compositions can also comprise adjuvants, such as, wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as, cocoa butter and polyethylene glycols which are solid at room temperature but liquid at bodytemperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium. Parenteral formulations containing rapamycin compounds are disclosed in U.S. Pat. Nos. 5,530,006, 5,516,770 and 5,626,588, the disclosures of each of which are incorporated by reference herein in their entirety.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances that increase the viscosity of the suspension and include, for example, sodium carboxymethyl cellulose, sorbitol and/or dextran. Optionally, the suspension may also contain stabilizers.

Solvents useful in the practice of this invention include pharmaceutically acceptable, water-miscible, non-aqueous solvents. In the context of this invention, these solvents should be taken to include solvents that are generally acceptable for pharmaceutical use, substantially water-miscible, and substantially non-aqueous. Preferably, these solvents are also non-phthalate plasticizer leaching solvents, so that, when used in medical equipment, they substantially do not leach phthalate plasticizers that may be present in the medical equipment. More preferably, the pharmaceutically-acceptable, water-miscible, non-aqueous solvents usable in the practice of this invention include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as, 2-ethoxyethyl acetate, methyl acetate, ethyl acetate, ethylene glycol diethyl ether, or ethylene glycol dimethyl ether; (S)-(−)-ethyl lactate; acetone; glycerol; alkyl ketones such as, methylethyl ketone or dimethyl sulfone; tetrahydrofuran; cyclic alkyl amides such as, caprolactam; decylmethylsulfoxide; oleic acid; aromatic amines such as, N,N-diethyl-m-toluamide; or 1-dodecylazacycloheptan-2-one.

The most preferred pharmaceutically-acceptable, water-miscible, non-aqueous solvents are N-methyl pyrrolidone (NMP), propylene glycol, ethyl acetate, dimethyl sulfoxide, dimethyl acetamide, benzyl alcohol, 2-pyrrolidone, or benzyl benzoate. Ethanol may also be used as a pharmaceutically-acceptable, water-miscible, non-aqueous solvent according to the invention, despite its negative impact on stability. Additionally, triacetin may also be used as a pharmaceutically-acceptable, water-miscible, non-aqueous solvent, as well as functioning as a solubilizer in certain circumstances. NMP may be available as PHARMASOLVE® from International Specialty Products (Wayne, N.J.). Benzyl alcohol may be available from J. T. Baker, Inc. Ethanol may be available from Spectrum, Inc. Triacetin may be available from Mallinkrodt, Inc.

The compositions of this invention can further include solubilizers. Solubilization is a phenomenon that enables the formation of a solution. It is related to the presence of amphiphiles, that is, those molecules that have the dual properties of being both polar and non-polar in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as, for example, PEG 300, PEG 400, or their blend with 3350, and the like), polysorbates (such as, for example, Polysorbate 20, Polysorbate 40, Polysorbate 60, Polysorbate 65, Polysorbate 80, and the like), poloxamers (such as, for example, Poloxamer 124, Poloxamer 188, Poloxamer 237, Poloxamer 338, Poloxamer 407, and the like), polyoxyethylene ethers (such as, for example, Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether, and the like), polyoxylstearates (such as, for example, Polyoxyl 30 stearate, Polyoxyl 40 stearate, Polyoxyl 50 stearate, Polyoxyl 100 stearate, and the like), polyethoxylated stearates (such as, for example, polyethoxylated 12-hydroxy stearate, and the like), and Tributyrin.

Other materials that may be added to the compositions of the invention include cyclodextrins, and cyclodextrin analogs and derivatives, and other soluble excipients that could enhance the stability of the inventive composition, maintain the product in solution, or prevent side effects associated with the administration of the inventive composition. Cyclodextrins may be available as ENCAPSIN® from Janssen Pharmaceuticals.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as, triglycerides. Oral formulations can include standard carriers such as, pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules, nanoparticles, and the like. The required dosage can be administered as a single unit or in a sustained release form.

The bioavailabilty of the compositions can be enhanced by micronization of the formulations using conventional techniques such as, grinding, milling, spray drying and the like in the presence of suitable excipients or agents such as, phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the invention may be of any configuration suitable for sustained release. Preferred sustained release therapeutic dosage forms exhibit one or more of the following characteristics: microparticles (e.g., from about 0.5 micrometers to about 100 micrometers in diameter, preferably about 0.5 to about 2 micrometers; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, preferably about 50 to about 250 nanometers; or from about 0.01 nanometer to about 1000 nanometers in diameter, preferably from about 50 to about 200 nanometers), free flowing powder structure; biodegradable structure designed to biodegrade over a period of time between from about 0.5 to about 180 days, preferably from about 1 to 3 to about 150 days, more preferably from about 3 to about 180 days, and most preferably from about 10 to about 21 days; or non-biodegradable structure to allow the therapeutic agent diffusion to occur over a time period of between from about 0.5 to about 180 days, more preferably from about 30 to about 120 days; or from about 3 to about 180 days, more preferably from about 10 to about 21 days; biocompatible with target tissue and the local physiological environment into which the dosage form to be administered, including yielding biocompatible biodegradation products; facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular or non-vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Preferred sustained release dosage forms of the invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

The compounds and compositions of the invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositons is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as, the activity, efficacy, pharmacokinetic and toxicology profiles of the particular compound used, whether a drug delivery system is used, and whether the compound is administered as part of a drug combination.

The usual doses of rapamycin compounds (including nitrosated and/or nitrosylated rapamycin compounds) for intraveneous dosages, can be, but is not limited to about 0.001 mg/kg/day to 25 mg/kg/day, preferably about 0.005 mg/kg/day to 5 mg/kg/day and more preferably about 0.01 mg/kg/day to 0.5 mg/kg/day. The usual doses of rapamycin compounds (including nitrosated and/or nitrosylated rapamycin compounds) for oral dosages, can be, but is not limited to about 0.005 mg/kg/day to 150 mg/kg/day, preferably about 0.05 mg/kg/day to 100 mg/kg/day and more preferably about 0.01 mg/kg/day to 10 mg/kg/day.

The doses of nitric oxide donors in the pharmaceutical composition will be dependent on the specific nitric oxide donor compound and the mode of administration. For example, when L-arginine is the orally administered nitric oxide donor, it can be administered in an amount of about 3 grams to about 15 grams to provide a plasma level in the range of about 0.2 mM to about 30 mM. When L-arginine is delivered directly at the site of injury by local administration, the L-arginine is delivered in an amount of at least about 50 mg to about 500 mg, preferably about 100 mg to about 2 g. the time of the treatment will usually be at least about 2 minutes to about 30 minutes, more preferably about 5 minutes to about 15 minutes.

The nitrosated and/or nitrosylated rapamycin compounds of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration, and is within the skill in the art.

The invention also provides pharmaceutical kits comprising one or more containers filled with one or more of the ingredients of the pharmaceutical compounds and/or compositions of the invention, including, one or more rapamycin compounds, optionally substituted with one or more NO and/or $NO_2$ groups, and one or more of the NO donors, and one or more therapeutic agents described herein. Such kits can also include, for example, other compounds and/or compositions (e.g., therapeutic agents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

The disclosure of each patent, patent application and publication cited or described in the specification is hereby incorporated by reference herein in its entirety.

Although the invention has been set forth in detail, one skilled in the art will appreciate that numerous changes and modifications may be made without departing from the spirit and scope of the invention.

What is claimed is:

1. A compound of Formula (I), Formula (II), a stereoisomer thereof and/or a pharmaceutically acceptable salt thereof, wherein the compound of Formula (I) is:

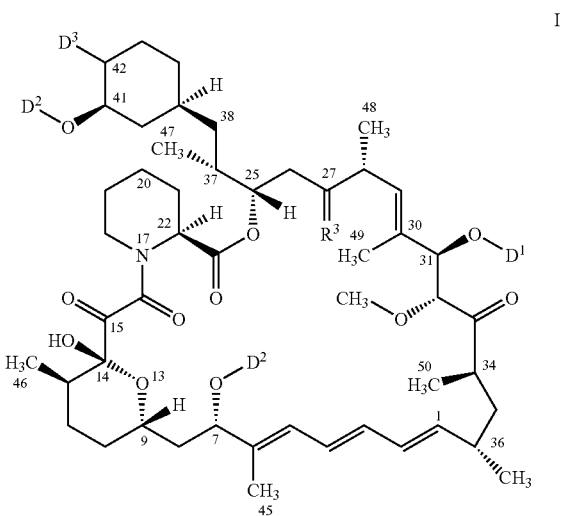

wherein:

$R^3$ is an oxygen, $N-OD^1$ or $N-NHD^1$;

$D^1$ is a hydrogen, V or K;

$D^2$ is a hydrogen, $-CH_3$, V or K;

$D^3$ is $-OD^1$, $-O-CH_2-CH_2-OD^1$,

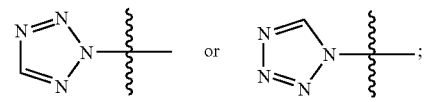

V is $-NO$ or $-NO_2$;

K is $-W_a-E_b-(C(R_e)(R_f))_p-E_c-(C(R_e)(R_f))_x-W_d-(C(R_e)(R_f))_y-W_i-E_j-W_g-(C(R_e)(R_f))_z-U-V$;

a, b, c, d, g, i and j are each independently an integer from 0 to 3;

p, x, y and z are each independently an integer from 0 to 10;

W at each occurrence is independently $-C(O)-$, $-C(S)-$, $-T-$, $-(C(R_e)(R_f))_h-$, an alkyl group, an aryl group, a heterocyclic ring, an arylheterocyclic ring, or $-(CH_2CH_2O)_q-$;

E at each occurrence is independently $-T-$, an alkyl group, an aryl group, $-(C(R_e)(R_f))_h-$, a heterocyclic ring, an arylheterocyclic ring, or $-(CH_2CH_2O)_q-$;

T at each occurrence is independently a covalent bond, a carbonyl, an oxygen, $-S(O)_o-$ or $-N(R_a)R_i$;

h is an integer form 1 to 10;

q is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, $W_h$, —$(CH_2)_o$—U—V, or —$(C(R_g)(R_h))_k$—U—V, or $R_e$ and $R_f$ taken together with the carbons to which they are attached form a carbonyl, a methanthial, a heterocyclic ring, a cycloalkyl group, an aryl group, an oxime, a hydrazone or a bridged cycloalkyl group;

$R_g$ and $R_h$ at each occurrence are independently $R_e$;

k is an integer from 1 to 3;

U at each occurrence is independently a covalent bond, a carbonyl, an oxygen, —$S(O)_o$— or —$N(R_a)R_i$;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—$C(U—V)(R_e)(R_f)$, a bond to an adjacent atom creating a double bond to that atom, —$(N_2O_2$—$)^-.M^+$, wherein $M^+$ is an organic or inorganic cation; and with the proviso that the compounds of Formula (I) must contain at least one NO group, or at least one $NO_2$ group; wherein the at least one NO group or the at least one $NO_2$ group is linked to the compound of Formula (I) through an oxygen atom, a nitrogen atom or a sulfur atom;

wherein the compound of Formula (II) is:

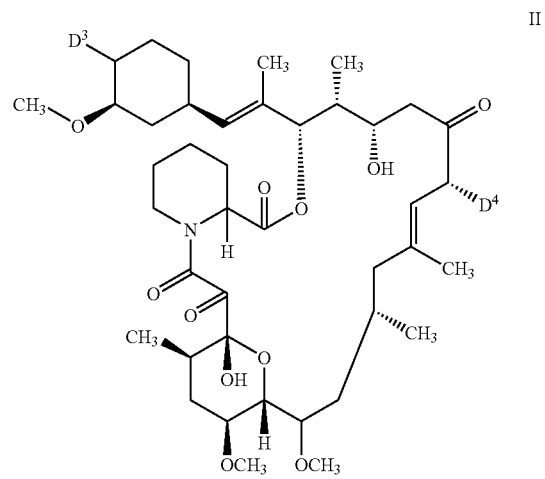

wherein:
$D^4$ is:

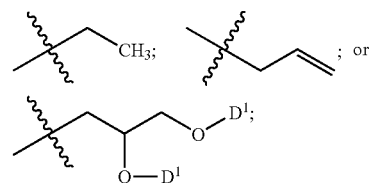

$D^1$ and $D^3$ are as defined herein; and with the proviso that the compounds of Formula (II) must contain at least one NO group, or at least one $NO_2$ group; wherein the at least one NO group or the at least one $NO_2$ group is linked to the compound of Formula (II) through an oxygen atom, a nitrogen atom or a sulfur atom.

2. The compound of claim 1, wherein the compound of Formula (I) is a nitrosated rapamycin, a nitrosylated rapamycin, a nitrosated and nitrosylated rapamycin, a nitrosated 42-deoxy-42-(1H-tetrazol-1-yl)-rapamycin, a nitrosylated 42-deoxy-42-(1H-tetrazol-1-yl)-rapamycin, a nitrosated and nitrosylated 42-deoxy-42-(1H-tetrazol-1-yl)-rapamycin, a nitrosated 42-deoxy-42-(2H-tetrazol-1-yl)-rapamycin, a nitrosylated 42-deoxy-42-(2H-tetrazol-1-yl)-rapamycin, a nitrosated and nitrosylated 42-deoxy-42-(2H-tetrazol-1-yl)-rapamycin, a nitrosated 42-O-(2-hydroxyethyl)-rapamycin, a nitrosylated 42-O-(2-hydroxyethyl)-rapamycin, a nitrosated and nitrosylated 42-O-(2-hydroxyethyl)-rapamycin and the compound of Formula (II) is a nitrosated tacrolimus, a nitrosylated tacrolimus, a nitrosated and nitrosylated tacrolimus, a nitrosated ascomycin, a nitrosylated ascomycin or a nitrosated and nitrosylated ascomycin.

3. A composition comprising at least one compound of claim 1 and a pharmaceutically acceptable carrier.

* * * * *